(12) United States Patent
Barth et al.

(10) Patent No.: US 7,632,852 B2
(45) Date of Patent: Dec. 15, 2009

(54) (1,5-DIPHENYL-1H-PYRAZOL-3-YL)OXADIAZOLE DERIVATIVES, PREPARATION METHOD THEREOF AND USE OF SAME IN THERAPEUTICS

(75) Inventors: Francis Barth, Saint Georges d'Orques (FR); Christian Congy, Saint Gely du Fesc (FR); Patrick Gueule, Teyran (FR); Murielle Rinaldi-Carmona, Saint Georges d'Orques (FR); Didier Van Broeck, Juvignac (FR)

(73) Assignee: Sanofi-aventis, Paris (FR)

( * ) Notice: Subject to any disclaimer, the term of this patent is extended or adjusted under 35 U.S.C. 154(b) by 27 days.

(21) Appl. No.: 11/835,670

(22) Filed: Aug. 8, 2007

(65) Prior Publication Data

US 2008/0039510 A1 Feb. 14, 2008

Related U.S. Application Data

(63) Continuation of application No. PCT/FR2006/000368, filed on Feb. 17, 2006.

(30) Foreign Application Priority Data

Feb. 21, 2005 (FR) .................... 05 01860

(51) Int. Cl.
*A61K 31/4155* (2006.01)
*A61K 31/4245* (2006.01)
*C07D 271/10* (2006.01)
*C07D 231/10* (2006.01)

(52) U.S. Cl. ............. 514/364; 514/406; 548/143; 548/364.1

(58) Field of Classification Search ........... 514/364, 514/403, 406; 548/131, 143, 373.1, 364.1
See application file for complete search history.

(56) References Cited

U.S. PATENT DOCUMENTS 7,183,306 B2 * 2/2007 Shirai et al. ............. 514/406
2004/0116475 A1 6/2004 Shirai et al.

FOREIGN PATENT DOCUMENTS

| WO | WO 98/32441 | 7/1998 |
| WO | WO 03/088968 | 10/2003 |
| WO | WO 2004/035566 | 4/2004 |
| WO | WO 2005/000820 | 1/2005 |

OTHER PUBLICATIONS

Vippagunta et al., Advanced Drug Delivery Reviews, p. 1.*
Vippagunta et al., Advanced Drug Delivery Reviews, vol. 48, p. 3-26, (2001).*
Maslivets, A. N., et. al., Five-Membered 2,3-Dioxoheterocycles. XI. Synthesis and Chemical Transformations of the Beta-Aroylhydrazides of Aroylpyruvic acids, J. Org. Chem. USSR. vol. 25, No. 5, (1989) pp. 935-940.

* cited by examiner

*Primary Examiner*—Yong Chu
(74) *Attorney, Agent, or Firm*—Balaram Gupta

(57) ABSTRACT

The invention relates to compounds having formula (I):

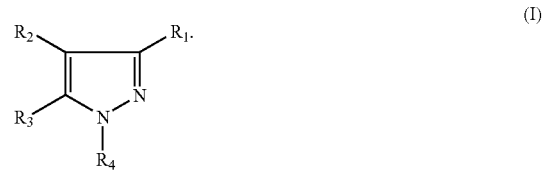

Wherein R1, R2, R3 and R4 are as defined herein. The invention also relates to a method of preparing said compounds and to the application thereof in therapeutics.

6 Claims, No Drawings

(1,5-DIPHENYL-1H-PYRAZOL-3-YL)OXADIAZOLE DERIVATIVES, PREPARATION METHOD THEREOF AND USE OF SAME IN THERAPEUTICS

CROSS REFERENCE TO RELATED APPLICATIONS

This application is a continuation of International application No. PCT/FR2006/000,368, filed Feb. 17, 2006, which is incorporated herein by reference in its entirety; which claims the benefit of priority of French Patent Application No. 05/01, 860, filed Feb. 21, 2005.

BACKGROUND OF THE INVENTION

1. Field of the Invention

The subject-matter of the present invention is (1,5-diphenyl-1H-pyrazol-3-yl)oxadiazole derivatives, their preparation and their application in therapeutics.

2. Description of the Art

Diphenylpyrazole derivatives exhibiting an affinity for $CB_1$ cannabinoid receptors have been disclosed in particular in Patents EP 0 576 357, EP 0 656 354 and U.S. Pat. No. 5,624,941 and in Application WO 2005/000 820.

2-(1,5-Diphenyl-1H-pyrazol-3-yl)-1,3,4-oxadiazole derivatives are described in J. Org. Chem. USSR, 1989, 25 (5), 935-940.

Novel (1,5-diphenyl-1H-pyrazol-3-yl)oxadiazole derivatives which possess antagonist properties for $CB_1$ cannabinoid receptors have now been found.

SUMMARY OF THE INVENTION

The subject-matter of the present invention is compounds corresponding to the formula (I):

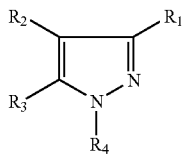

(I)

in which:

$R_I$ represents a heterocyclic radical chosen from:

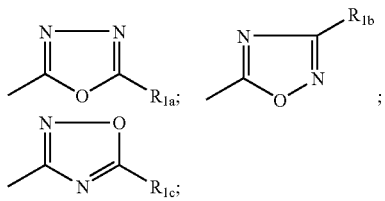

$R_{1a}$ represents:
- a $(C_1-C_7)$alkyl which is unsubstituted or substituted by:
  a) one or more halogen atoms;
  b) a $(C_1-C_4)$alkoxy, a trifluoromethoxy or a phenoxy;
  c) a phenyl which is unsubstituted or mono-, di- or trisubstituted by substituents chosen independently from a halogen atom, a $(C_1-C_4)$alkyl, a $(C_1-C_4)$alkoxy, a trifluoromethyl radical or a trifluoromethoxy radical;
  d) an aromatic heterocyclic radical chosen from a thienyl, a pyrrolyl, an imidazolyl, a furyl or a pyrazolyl;
- a nonaromatic $C_3-C_{12}$ carbocyclic radical which is unsubstituted or substituted one or more times by a $(C_1-C_4)$alkyl;
- a phenyl which is unsubstituted or mono-, di- or trisubstituted by substituents chosen independently from a halogen atom, a $(C_1-C_4)$alkyl, a $(C_1-C_4)$alkoxy, a trifluoromethyl radical or a trifluoromethoxy radical;
- an $—NR_5R_6$ group;
- an $—NR_7COR_8$ group;
- a $—COOR_9$ group;
- a $—CONR_{10}R_{11}$ group;
- an $—S—R_{12}$ group;
- an $—S(O)_mR_{13}$ group in which m is 1 or 2;
- an $—O—R_{14}$ group;

$R_{1b}$ represents:
- a $(C_1-C_7)$alkyl which is unsubstituted or substituted by:
  a) one or more halogen atoms;
  b) a $(C_1-C_4)$alkoxy, a trifluoromethoxy or a phenoxy;
  c) a phenyl which is unsubstituted or mono-, di- or trisubstituted by substituents chosen independently from a halogen atom, a $(C_1-C_4)$alkyl, a $(C_1-C_4)$alkoxy, a trifluoromethyl radical or a trifluoromethoxy radical;
  d) an aromatic heterocyclic radical chosen from a thienyl, a pyrrolyl, an imidazolyl, a furyl or a pyrazolyl;
- a nonaromatic $C_3-C_{12}$ carbocyclic radical which is unsubstituted or substituted one or more times by a $(C_1-C_4)$alkyl;
- a phenyl which is unsubstituted or mono-, di- or trisubstituted by substituents chosen independently from a halogen atom, a $(C_1-C_4)$alkyl, a $(C_1-C_4)$alkoxy, a trifluoromethyl radical or a trifluoromethoxy radical;
- an $—NR_{15}R_{16}$ group;
- an $—NR_7COR_8$ group;

$R_{1c}$ represents:
- a $(C_1-C_7)$alkyl which is unsubstituted or substituted by:
  a) one or more halogen atoms;
  b) a $(C_1-C_4)$alkoxy, a trifluoromethoxy or a phenoxy;
  c) a phenyl which is unsubstituted or mono-, di- or trisubstituted by substituents chosen independently from a halogen atom, a $(C_1-C_4)$alkyl, a $(C_1-C_4)$alkoxy, a trifluoromethyl radical or a trifluoromethoxy radical;
  d) an aromatic heterocyclic radical chosen from a thienyl, a pyrrolyl, an imidazolyl, a furyl or a pyrazolyl;
- a nonaromatic $C_3-C_{12}$ carbocyclic radical which is unsubstituted or substituted one or more times by a $(C_1-C_4)$alkyl;
- a phenyl which is unsubstituted or mono-, di- or trisubstituted by substituents chosen independently from a halogen atom, a $(C_1-C_4)$alkyl, a $(C_1-C_4)$alkoxy, a trifluoromethyl radical or a trifluoromethoxy radical;
- an $—NR_{15}R_{16}$ group;
- an $—NR_7COR_8$ group;

$R_2$ represents a $(C_1-C_5)$alkyl or a cyano;

$R_3$ represents a phenyl which is unsubstituted or mono-, di- or trisubstituted by substituents chosen independently from a halogen atom, a $(C_1-C_4)$alkyl, a $(C_1-C_4)$alkoxy, a trifluoromethyl radical, a trifluoromethoxy radical or an $S(O)_n$Alk group;

$R_4$ represents a phenyl which is unsubstituted or mono-, di- or trisubstituted by substituents chosen independently from a halogen atom, a $(C_1-C_4)$alkyl, a $(C_1-C_4)$alkoxy, a trifluoromethyl radical, a trifluoromethoxy radical or an $S(O)_n$Alk group;

$R_5$ and $R_6$ each independently represent a hydrogen atom or a $(C_1-C_4)$alkyl;

or else $R_5$ and $R_6$, together with the nitrogen atom to which they are bonded, constitute a heterocyclic radical chosen from azetidine, pyrrolidine, piperidine or morpholine;

$R_7$ represents a hydrogen atom or a $(C_1-C_3)$alkyl;

$R_8$ represents a $(C_1-C_4)$alkyl;

$R_9$ represents a $(C_1-C_4)$alkyl;

$R_{10}$ and $R_{11}$ each independently represent a hydrogen atom, a $(C_1-C_4)$alkyl or a benzyl;

or else $R_{10}$ and $R_{11}$, together with the nitrogen atom to which they are bonded, constitute a heterocyclic radical chosen from azetidine, pyrrolidine, piperidine or morpholine;

$R_{12}$ represents a hydrogen atom, a $(C_1-C_7)$alkyl, a $(C_3-C_7)$cycloalkyl, a $(C_3-C_7)$cycloalkylmethyl, a benzyl or a phenethyl;

$R_{13}$ represents a $(C_1-C_7)$alkyl, a $(C_3-C_7)$cycloalkyl, a $(C_3-C_7)$cycloalkylmethyl, a benzyl or a phenethyl;

$R_{14}$ represents a $(C_1-C_7)$alkyl or a phenyl which is unsubstituted or mono-, di- or trisubstituted by substituents chosen independently from a halogen atom, a $(C_1-C_4)$alkyl, a $(C_1-C_4)$alkoxy, a trifluoromethyl radical or a trifluoromethoxy radical;

$R_{15}$ and $R_{16}$ each independently represent a hydrogen atom or a $(C_1-C_4)$alkyl;

n represents 0, 1 or 2;

Alk represents a $(C_1-C_4)$alkyl.

The compounds of formula (I) can comprise one or more asymmetric carbon atoms. They can thus exist in the form of enantiomers or of diastereoisomers. These enantiomers, diastereoisomers and their mixtures, including the racemic mixtures, form part of the invention.

The compounds of formula (I) can exist in the form of hydrates or of solvates, namely in the form of combinations or associations with one or more water molecules or with a solvent. Such hydrates and solvates also form part of the invention.

DETAILED DESCRIPTION OF THE INVENTION

The term "halogen atom" is understood to mean a bromine, chlorine, fluorine or iodine atom.

The term "$(C_1-C_3)$alkyl" or respectively "$(C_1-C_4)$alkyl", "$(C_1-C_5)$alkyl" or "$(C_1-C_7)$alkyl" is understood to mean a linear or branched alkyl radical comprising one to three carbon atoms or respectively comprising one to four carbon atoms, comprising one to five carbon atoms or comprising one to seven carbon atoms, such as the methyl, ethyl, propyl, isopropyl, butyl, isobutyl, sec-butyl, tert-butyl, pentyl, isopentyl, hexyl, isohexyl or heptyl radical.

The term "$(C_1-C_4)$alkoxy" is understood to mean a linear or branched alkoxy radical comprising one to four carbon atoms, such as the methoxy, ethoxy, propoxy, isopropoxy, butoxy, sec-butoxy or tert-butoxy radical.

The term "$(C_3-C_7)$cycloalkyl" is understood to mean a cyclic alkyl group of 3 to 7 carbon atoms, such as the cyclopropyl, cyclobutyl, cyclopentyl, cyclohexyl or cycloheptyl group.

The nonaromatic $C_3-C_{12}$ carbocyclic radicals comprise monocyclic or condensed, bridged or spiro polycyclic radicals. The monocyclic radicals include cycloalkyls, for example cyclopropyl, cyclobutyl, cyclopentyl, cyclohexyl, cycloheptyl or cyclooctyl. The condensed, bridged or spiro di- or tricyclic radicals include, for example, the norbornyl, bornyl, isobornyl, noradamantyl, adamantyl, spiro[5.5]undecyl, bicyclo[2.2.1]heptyl, bicyclo[3.2.1]octyl or bicyclo [3.1.1]heptyl radicals.

The following are singled out among the compounds of formula (I) which are subject-matters of the invention:

the compounds of formula (IA) in which $R_I$ represents a radical:

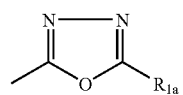

and the substituents $R_{1a}$, $R_2$, $R_3$ and $R_4$ are as defined for the compounds of formula (I);

the compounds of formula (IB) in which $R_I$ represents a radical:

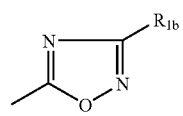

and the substituents $R_{1b}$, $R_2$, $R_3$ and $R_4$ are as defined for the compounds of formula (I);

the compounds of formula (IC) in which $R_I$ represents a radical:

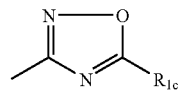

and the $R_{1c}$, $R_2$, $R_3$ and $R_4$ substituents are as defined for the compounds of formula (I).

According to the present invention, preference is given to the compounds of formula (I) in which:

$R_I$ represents a radical:

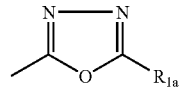

$R_{1a}$ represents:

a $(C_1-C_7)$alkyl which is unsubstituted or substituted by a phenyl which is itself unsubstituted or mono-, di- or trisubstituted by substituents chosen independently from a halogen atom, a $(C_1-C_4)$alkyl, a $(C_1-C_4)$alkoxy, a trifluoromethyl radical or a trifluoromethoxy radical;

a nonaromatic $C_3-C_{12}$ carbocyclic radical which is unsubstituted or substituted one or more times by a $(C_1-C_4)$alkyl;

a phenyl which is unsubstituted or mono-, di- or trisubstituted by substituents chosen independently from a halogen atom, a (C₁-C₄)alkyl, a (C₁-C₄)alkoxy, a trifluoromethyl radical or a trifluoromethoxy radical;
an —NR₅R₆ group;
an —NR₇COR₈ group;
R₂ represents a (C₁-C₅)alkyl or a cyano;
R₃ represents a phenyl which is unsubstituted or mono-, di- or trisubstituted by substituents chosen independently from a halogen atom, a (C₁-C₄)alkyl, a (C₁-C₄)alkoxy, a trifluoromethyl radical, a trifluoromethoxy radical or an S(O)ₙAlk group;
R₄ represents a phenyl which is unsubstituted or mono-, di- or trisubstituted by substituents chosen independently from a halogen atom, a (C₁-C₄)alkyl, a (C₁-C₄)alkoxy, a trifluoromethyl radical, a trifluoromethoxy radical or an S(O)ₙAlk group;
R₅ and R₆ each independently represent a hydrogen atom or a (C₁-C₄)alkyl;
or else R₅ and R₆, together with the nitrogen atom to which they are bonded, constitute a heterocyclic radical chosen from azetidine, pyrrolidine, piperidine or morpholine;
R₇ represents a hydrogen atom or a (C₁-C₃)alkyl;
R₈ represents a (C₁-C₄)alkyl;
n represents 0, 1 or 2;
Alk represents a (C₁-C₄)alkyl;

in the base form and in the hydrate or solvate form.

Among the compounds of formula (I) which are subject-matters of the invention, a first group of compounds is composed of the compounds for which:
R₁ represents a heterocyclic radical chosen from:

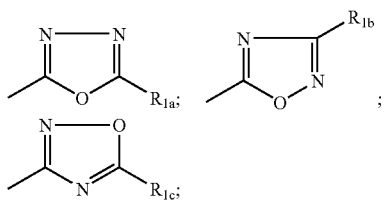

R₁ₐ represents:
a methyl, a propyl, an isopropyl, a 1,1-dimethylpropyl, a 1-ethylpropyl, a 3-phenylpropyl, an isobutyl, a tert-butyl, a 1-propylbutyl, a 1-(4-chlorophenyl)-1-methylethyl, a 2-phenylethyl, a 2-(3-fluorophenyl)ethyl, a 2-(3-chlorophenyl)ethyl, a benzyl, a 3-(4-methoxyphenyl)propyl, a 4-phenylbutyl, a 2-phenoxyethyl, a (2-thienyl)methyl, a 2-(2-thienyl)ethyl or a 3-(2-thienyl)propyl;
a cyclopropyl, a cyclobutyl, a cyclohexyl or a 1-adamantyl;
a 3-(trifluoromethyl)phenyl;
an amino, a dimethylamino or a piperid-1-yl;
an acetylamino or a pivaloylamino;
an ethoxycarbonyl;
a tert-butylaminocarbonyl, a diethylaminocarbonyl, a benzylaminocarbonyl or a piperid-1-ylcarbonyl;
a mercapto, an isopropylthio, an isobutylthio, a (1-ethylpropyl)thio, a (cyclopropylmethyl)thio, a benzylthio or a 2-phenylethylthio;
a benzylsulfinyl, a (2-phenylethyl)sulfinyl, an isopropylsulfonyl, a (1-ethylpropyl)sulfonyl, a (cyclopropylmethyl)sulfonyl, a benzylsulfonyl or a (2-phenylethyl)sulfonyl;

R₁ᵦ represents:
an isopropyl or a tert-butyl;
R₁c represents:
a tert-butyl, a 2-phenylethyl or a 2-(2-thienyl)ethyl;
R₂ represents a methyl, an ethyl or a cyano;
R₃ represents a 4-bromophenyl or a 4-chlorophenyl;
R₄ represents a 2-chlorophenyl or a 2,4-dichlorophenyl;

and their hydrates or their solvates.

Among the compounds of formula (IA) which are subject-matters of the invention, another group of compounds is composed of the compounds for which:
R₁ represents a radical:

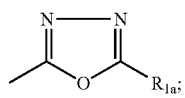

R₁ₐ represents:
a methyl, a propyl, an isopropyl, a 1,1-dimethylpropyl, a 1-ethylpropyl, a 3-phenylpropyl, an isobutyl, a tert-butyl, a 1-propylbutyl, a 1-(4-chlorophenyl)-1-methylethyl, a 2-phenylethyl, a 2-(3-fluorophenyl)ethyl, a 2-(3-chlorophenyl)ethyl, a benzyl, a 3-(4-methoxyphenyl)propyl, a 4-phenylbutyl, a 2-phenoxyethyl, a (2-thienyl)methyl, a 2-(2-thienyl)ethyl or a 3-(2-thienyl)propyl;
a cyclopropyl, a cyclobutyl, a cyclohexyl or a 1-adamantyl;
a 3-(trifluoromethyl)phenyl;
an amino, a dimethylamino or a piperid-1-yl;
an acetylamino or a pivaloylamino;
an ethoxycarbonyl;
a tert-butylaminocarbonyl, a diethylaminocarbonyl, a benzylaminocarbonyl or a piperid-1-ylcarbonyl;
a mercapto, an isopropylthio, an isobutylthio, a (1-ethylpropyl)thio, a (cyclopropylmethyl)thio, a benzylthio or a 2-phenylethylthio;
a benzylsulfinyl, a (2-phenylethyl)sulfinyl, an isopropylsulfonyl, a (1-ethylpropyl)sulfonyl, a (cyclopropylmethyl)sulfonyl, a benzylsulfonyl or a (2-phenylethyl)sulfonyl;
R₂ represents a methyl, an ethyl or a cyano;
R₃ represents a 4-bromophenyl or a 4-chlorophenyl;
R₄ represents a 2-chlorophenyl or a 2,4-dichlorophenyl;

and their hydrates or their solvates.

Among the compounds of formula (IB) which are subject-matters of the invention, another group of compounds is composed of the compounds for which:
R₁ represents a radical:

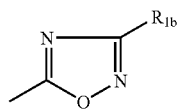

R₁ᵦ represents:
an isopropyl or a tert-butyl;
R₂ represents a methyl;
R₃ represents a 4-chlorophenyl;
R₄ represents a 2,4-dichlorophenyl;

and their hydrates or their solvates.

Among the compounds of formula (IC) which are subject-matters of the invention, another group of compounds is composed of the compounds for which:

R$_I$ represents a radical:

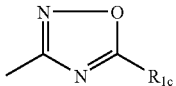

R$_{1c}$ represents:
  a tert-butyl, a 2-phenylethyl or a 2-(2-thienyl)ethyl;
R$_2$ represents a methyl;
R$_3$ represents a 4-chlorophenyl;
R$_4$ represents a 2,4-dichlorophenyl;

and their hydrates or their solvates.

Mention may be made, among the compounds of formula (I), of the compounds of formula (I) for which:
R$_I$ represents a radical:

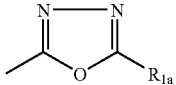

R$_{1a}$ represents:
  a methyl, a propyl, an isopropyl, a 1,1-dimethylpropyl, a 1-ethylpropyl, a 3-phenylpropyl, an isobutyl, a tert-butyl, a 1-propylbutyl or a 1-(4-chlorophenyl)-1-methylethyl;
  a cyclopropyl, a cyclobutyl, a cyclohexyl or a 1-adamantyl;
  a 3-(trifluoromethyl)phenyl;
  an amino or a dimethylamino;
  an acetylamino or a pivaloylamino;
  a piperidin-1-yl;
R$_2$ represents a methyl, an ethyl or a cyano;
R$_3$ represents a 4-bromophenyl or a 4-chlorophenyl;
R$_4$ represents a 2-chlorophenyl or a 2,4-dichlorophenyl;

and their hydrates or their solvates.

Mention may in particular be made, among the compounds of formula (I) which are subject-matters of the invention, of the following compounds:

2-(tert-butyl)-5-[1-(2-chlorophenyl)-5-(4-chlorophenyl)-4-methyl-1H-pyrazol-3-yl]-1,3,4-oxadiazole;
2-[1-(2-chlorophenyl)-5-(4-chlorophenyl)-4-methyl-1H-pyrazol-3-yl]-5-isopropyl-1,3,4-oxadiazole;
2-(tert-butyl)-5-[5-(4-chlorophenyl)-1-(2,4-dichlorophenyl)-4-methyl-1H-pyrazol-3-yl]-1,3,4-oxadiazole;
2-[5-(4-chlorophenyl)-1-(2,4-dichlorophenyl)-4-methyl-1H-pyrazol-3-yl]-5-isopropyl-1,3,4-oxadiazole;
2-[5-(4-chlorophenyl)-1-(2,4-dichlorophenyl)-4-methyl-1H-pyrazol-3-yl]-5-isobutyl-1,3,4-oxadiazole;
2-[5-(4-chlorophenyl)-1-(2,4-dichlorophenyl)-4-methyl-1H-pyrazol-3-yl]-5-(1-ethylpropyl)-1,3,4-oxadiazole;
2-[5-(4-chlorophenyl)-1-(2,4-dichlorophenyl)-4-methyl-1H-pyrazol-3-yl]-5-(3-phenylpropyl)-1,3,4-oxadiazole;
2-[5-(4-chlorophenyl)-1-(2,4-dichlorophenyl)-4-methyl-1H-pyrazol-3-yl]-5-cyclohexyl-1,3,4-oxadiazole;
2-(1-adamantyl)-5-[5-(4-chlorophenyl)-1-(2,4-dichlorophenyl)-4-methyl-1H-pyrazol-3-yl]-1,3,4-oxadiazole;
1-[5-[5-(4-chlorophenyl)-1-(2,4-dichlorophenyl)-4-methyl-1H-pyrazol-3-yl]-1,3,4-oxadiazol-2-yl]piperidine;
5-[5-(4-chlorophenyl)-1-(2,4-dichlorophenyl)-4-methyl-1H-pyrazol-3-yl]-1,3,4-oxadiazol-2-amine;
N-5-[5-(4-chlorophenyl)-1-(2,4-dichlorophenyl)-4-methyl-1H-pyrazol-3-yl]-1,3,4-oxadiazol-2-yl]acetamide;
N-[5-[5-(4-chlorophenyl)-1-(2,4-dichlorophenyl)-4-methyl-1H-pyrazol-3-yl]-1,3,4-oxadiazol-2-yl]-2,2-dimethylpropanamide;
2-[5-(4-bromophenyl)-1-(2,4-dichlorophenyl)-4-ethyl-1H-pyrazol-3-yl]-5-methyl-1,3,4-oxadiazole;
2-[5-(4-bromophenyl)-1-(2,4-dichlorophenyl)-4-ethyl-1H-pyrazol-3-yl]-5-isopropyl-1,3,4-oxadiazole;
2-[5-(4-bromophenyl)-1-(2,4-dichlorophenyl)-4-ethyl-1H-pyrazol-3-yl]-5-(tert-butyl)-1,3,4-oxadiazole;
2-[5-(4-bromophenyl)-1-(2,4-dichlorophenyl)-4-ethyl-1H-pyrazol-3-yl]-5-(1-propylbutyl)-1,3,4-oxadiazole;
2-[5-(4-bromophenyl)-1-(2,4-dichlorophenyl)-4-ethyl-1H-pyrazol-3-yl]-5-(1,1-dimethylpropyl)-1,3,4-oxadiazole;
2-[5-(4-bromophenyl)-1-(2,4-dichlorophenyl)-4-ethyl-1H-pyrazol-3-yl]-5-(3-phenylpropyl)-1,3,4-oxadiazole;
2-[5-(4-bromophenyl)-1-(2,4-dichlorophenyl)-4-ethyl-1H-pyrazol-3-yl]-5-[1-(4-chlorophenyl)-1-methylethyl]-1,3,4-oxadiazole;
2-[5-(4-bromophenyl)-1-(2,4-dichlorophenyl)-4-ethyl-1H-pyrazol-3-yl]-5-cyclopropyl-1,3,4-oxadiazole;
2-[5-(4-bromophenyl)-1-(2,4-dichlorophenyl)-4-ethyl-1H-pyrazol-3-yl]-5-cyclobutyl-1,3,4-oxadiazole;
2-[5-(4-bromophenyl)-1-(2,4-dichlorophenyl)-4-ethyl-1H-pyrazol-3-yl]-5-[3-(trifluoromethyl)phenyl]-1,3,4-oxadiazole;
2-[5-(4-bromophenyl)-1-(2,4-dichlorophenyl)-4-ethyl-1H-pyrazol-3-yl]-N,N-dimethyl-1,3,4-oxadiazole-2-amine;
5-(4-chlorophenyl)-1-(2,4-dichlorophenyl)-3-(5-propyl-1,3,4-oxadiazol-2-yl)-1H-pyrazole-4-carbonitrile;
5-(4-chlorophenyl)-1-(2,4-dichlorophenyl)-3-(5-isopropyl-1,3,4-oxadiazol-2-yl)-1H-pyrazole-4-carbonitrile;
3-(5-(tert-butyl)-1,3,4-oxadiazol-2-yl)-5-(4-chlorophenyl)-1-(2,4-dichlorophenyl)-1H-pyrazole-4-carbonitrile;
5-(4-chlorophenyl)-1-(2,4-dichlorophenyl)-3-[5-(3-phenylpropyl)-1,3,4-oxadiazol-2-yl]-1H-pyrazole-4-carbonitrile;
5-(4-chlorophenyl)-3-(5-cyclopropyl-1,3,4-oxadiazol-2-yl)-1-(2,4-dichlorophenyl)-1H-pyrazole-4-carbonitrile;
5-(4-bromophenyl)-1-(2,4-dichlorophenyl)-3-(5-isopropyl-1,3,4-oxadiazol-2-yl)-1H-pyrazole-4-carbonitrile;
5-(4-bromophenyl)-3-(5-(tert-butyl)-1,3,4-oxadiazol-2-yl)-1-(2,4-dichlorophenyl)-1H-pyrazole-4-carbonitrile;
5-(4-bromophenyl)-1-(2,4-dichlorophenyl)-3-(5-(3-phenylpropyl)-1,3,4-oxadiazol-2-yl]-1H-pyrazole-4-carbonitrile;
2-[5-(4-chlorophenyl)-1-(2,4-dichlorophenyl)-4-methyl-1H-pyrazol-3-yl]-5-(2-phenylethyl)-1,3,4-oxadiazole;
2-[5-(4-bromophenyl)-1-(2,4-dichlorophenyl)-4-ethyl-1H-pyrazol-3-yl]-5-[2-(2-thienyl)ethyl]-1,3,4-oxadiazole;
2-[5-(4-bromophenyl)-1-(2,4-dichlorophenyl)-4-ethyl-1H-pyrazol-3-yl]-5-(isobutylthio)-1,3,4-oxadiazole;
2-[5-(4-bromophenyl)-1-(2,4-dichlorophenyl)-4-ethyl-1H-pyrazol-3-yl]-5-[(cyclopropylmethyl)thio]-1,3,4-oxadiazole;
5-[5-(4-chlorophenyl)-1-(2,4-dichlorophenyl)-4-methyl-1H-pyrazol-3-yl]-3-isopropyl-1,2,4-oxadiazole;
3-(tert-butyl)-5-[5-(4-chlorophenyl)-1-(2,4-dichlorophenyl)-4-methyl-1H-pyrazol-3-yl]-1,2,4-oxadiazole;
5-(tert-butyl)-3-[5-(4-chlorophenyl)-1-(2,4-dichlorophenyl)-4-methyl-1H-pyrazol-3-yl]-1,2,4-oxadiazole;
3-[5-(4-chlorophenyl)-1-(2,4-dichlorophenyl)-4-methyl-1H-pyrazol-3-yl]-5-(2-phenylethyl)-1,2,4-oxadiazole;

3-[5-(4-chlorophenyl)-1-(2,4-dichlorophenyl)-4-methyl-1H-pyrazol-3-yl]-5-[2-(2-thienyl)ethyl]-1,2,4-oxadiazole;

and their hydrates or their solvates.

In that which follows, the term "protective group Pg" is understood to mean a group which makes it possible, on the one hand, to protect a reactive functional group, such as a hydroxyl or an amine, during a synthesis and, on the other hand, to regenerate the intact reactive functional group at the end of the synthesis. Examples of protective groups and of the protecting and deprotecting methods are given in "Protective Groups in Organic Synthesis", Green et al., 2$^{nd}$ Edition (John Wiley & Sons Inc., New York), 1991.

The term "leaving group" is understood to mean, in that which follows, a group which can be easily cleaved from a molecule by breaking a heterolytic bond, with departure of an electron pair. This group can thus be easily replaced by another group during a substitution reaction, for example. Such leaving groups are, for example, halogens or an activated hydroxyl group, such as a methanesulfonate, benzenesulfonate, p-toluenesulfonate, triflate, acetate, and the like. Examples of leaving groups and of the references for their preparation are given in "Advances in Organic Chemistry", J. March, 3$^{rd}$ Edition, Wiley Interscience, 1985, p. 310-316.

In accordance with the invention, it is possible to prepare the compounds of formula (I) according to the following processes.

In accordance with the invention, the compounds of formula (I) in
which

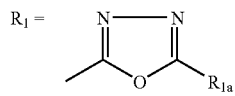

can be prepared according to a process which is characterized in that a compound of formula:

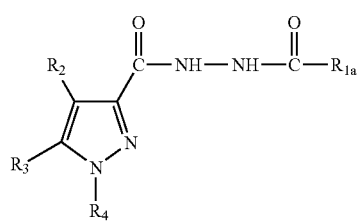

(II)

in which $R_{1a}$, $R_2$, $R_3$ and $R_4$ are as defined for a compound of formula (I), is cyclized.

The cyclization reaction is carried out generally in the presence of a catalytic amount of an acid, such as 4-toluenesulphonic acid, in a solvent, such as toluene, at a temperature between ambient temperature and the reflux temperature of the solvent and while removing the water formed by azeotropic distillation.

According to an alternative form of the process, the cyclization is carried out by reaction of the compound of formula (II) with 4-toluenesulphonyl chloride in the presence of a base, such as triethylamine, in a solvent, such as dichloromethane, and at a temperature between ambient temperature and the reflux temperature of the solvent.

According to another alternative form of the process, the cyclization is carried out in the presence of phosphorus oxychloride according to the process described in J. Org. Chem. USSR, 1989, 25 (5), 935-940.

Specifically, a compound of formula (I) in which $R_{1a}=NH_2$ can be prepared by reaction of a compound of formula:

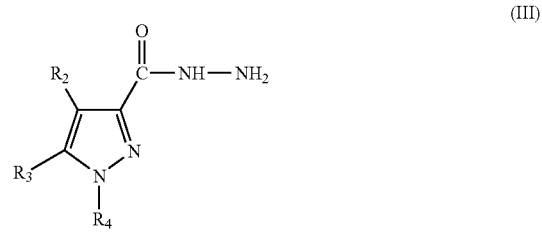

(III)

in which $R_2$, $R_3$ and $R_4$ are as defined for a compound of formula (I), with cyanogen bromide in a solvent, such as ethanol, at a temperature between ambient temperature and the reflux temperature of the solvent, followed by hydrolysis in a basic medium.

Also specifically, a compound of formula (I) in which $R_{1a}=NR_5R_6$ can be prepared by reaction of a compound of formula (III) with a compound of formula:

(IV)

in which $R_5$ and $R_6$ are as defined for a compound of formula (I) and Hal represents a halogen atom, in the presence of a base, such as triethylamine, in a solvent, such as dichloromethane, at a temperature between ambient temperature and the reflux temperature of the solvent.

Also specifically, a compound of formula (I) in which $R_{1a}=NR_7COR_8$ can be prepared by reaction of a compound of formula (I) in which $R_{1a}=NHR_7$ with an acid or a functional derivative of this acid of formula:

HOOC—R$_8$ (V)

in which $R_8$ is as defined for a compound of formula (I).

When the acid of formula (V) itself is used, the preparation is carried out in the presence of a coupling agent used in peptide chemistry, such as 1,3-dicyclohexylcarbodiimide or (benzotriazol-1-yloxy)tris(dimethylamino)-phosphonium hexafluorophosphate or (benzotriazol-1-yloxy)tris(pyrrolidino)-phosphonium hexafluorophosphate or 2-(1H-benzotriazol-1-yl)-1,1,3,3-tetramethyl-uronium tetrafluoroborate, in the presence of a base, such as triethylamine, N,N-diisopropylethylamine or 4-dimethylaminopyridine, in a solvent, such as dichloromethane, dichloroethane, N,N-dimethylformamide or tetrahydrofuran at a temperature between −10° C. and the reflux temperature of the solvent.

Use may be made, as functional derivative of the acid (V), of the acid chloride, the anhydride, a mixed anhydride, a $C_1$-$C_4$ alkyl ester in which the alkyl is straight or branched, or an activated ester, for example the p-nitrophenyl ester.

Thus, the chloride of the acid, obtained by reaction of thionyl chloride or oxalyl chloride with the acid of formula (V), can also be reacted with the compound of formula (I: $R_{1a}$=NHR$_7$) in a solvent, such as a chlorinated solvent (dichloromethane, dichloroethane or chloroform, for example), an ether (tetrahydrofuran or dioxane, for example) or an amide (N,N-dimethylformamide, for example), under an inert atmosphere, at a temperature between 0° C. and ambient temperature, in the presence of a tertiary amine, such as triethylamine, N-methylmorpholine or pyridine.

An alternative form consists in preparing the mixed anhydride of the acid of formula (V) by reaction of ethyl chloroformate with the acid of formula (V) in the presence of a base, such as triethylamine, and in reacting it with the compound of formula (I: $R_{1a}$=NHR$_7$) in a solvent, such as dichloromethane, under an inert atmosphere, at ambient temperature, in the presence of a base, such as triethylamine.

Also specifically, a compound of formula (I) in which $R_{1a}$=—CONR$_{10}$R$_{11}$ can be prepared by reaction of a compound of formula (I) in which $R_{1a}$=—COOEt with an amine of formula:

HNR$_{10}$R$_{11}$ (IX)

in which $R_{10}$ and $R_{11}$ are as defined for a compound of formula (I), in a solvent, such as dioxane, at the reflux temperature of the solvent.

Also specifically, a compound of formula (I) in which $R_{1a}$=—SH can be prepared by reaction of a compound of formula (III) with carbon disulphide in the presence of a base, such as potassium hydroxide, in a solvent, such as ethanol or pyridine, at the reflux temperature of the solvent.

Also specifically, a compound of formula (I) in which $R_{1a}$=—SR$_{12}$ with $R_{12}\neq$H can be prepared by reaction of a compound in which $R_{1a}$=—SH with a compound of formula:

Hal—R$_{12}$ (X)

in which $R_{12}$ is as defined for a compound of formula (I) and Hal represents a halogen atom, in the presence of a base, such as potassium carbonate, in a solvent, such as N, N-dimethylformamide, and at a temperature between ambient temperature and the reflux temperature of the solvent.

Also specifically, a compound of formula (I) in which $R_{1a}$=—S(O)$_m$R$_{13}$ can be prepared by reaction of the corresponding compounds of formula (I) in which $R_{1a}$=—SR$_{12}$ with an oxidizing agent, such as 3-chloroperbenzoic acid, in a solvent, such as dichloromethane, and at ambient temperature. By varying the amounts of acid used, either the sulfinyl derivatives ($R_{1a}$=—SO—R$_{13}$) or the sulfonyl derivatives ($R_{1a}$=—SO$_2$—R$_{13}$) are obtained.

Finally, specifically, the compounds of formula (I) in which $R_{1a}$=—OR$_{14}$ are prepared using the processes described in J. Heterocycl. Chem., 1973, 10, 989-991.

In accordance with the invention, the compounds of formula (I)

in which

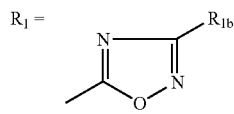

can be prepared according to a process which is characterized in that a compound of formula:

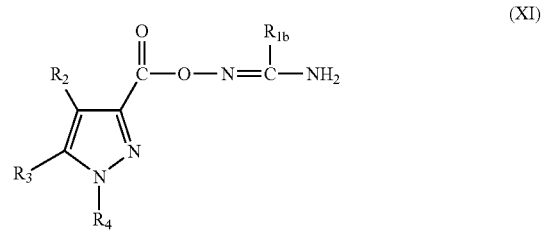

in which $R_{1b}$, $R_2$, $R_3$ and $R_4$ are as defined for a compound of formula (I), is cyclized.

The cyclization reaction is carried out generally in a solvent, such as n-butanol, and at a temperature between ambient temperature and the reflux temperature of the solvent.

Specifically, a compound of formula (I) in which $R_{1b}$=—NR$_{15}$R$_{16}$ in which $R_{15}$ and/or $R_{16}$ represent a (C$_1$-C$_4$)alkyl can be prepared by reaction of a compound of formula (I) in which $R_{1b}$=—NH$_2$ with a (C$_1$-C$_4$)alkyl halide in the presence of a base, such as sodium hydride, in a solvent, such as N,N-dimethylformamide, and at a temperature between ambient temperature and the reflux temperature of the solvent. Likewise, the compounds of formula (I) in which $R_{1b}$=—NR$_7$COR$_8$ are prepared by reaction with a compound of formula R$_8$COHal in which Hal represents a halogen atom in the presence of a base, such as pyridine or triethylamine, in a solvent, such as dichloromethane or N,N-dimethylformamide, at a temperature between ambient temperature and the reflux temperature of the solvent.

In accordance with the invention, the compounds of formula (I) in in which

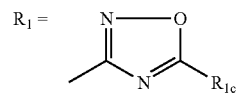

can be prepared according to a process which is characterized in that a compound of formula:

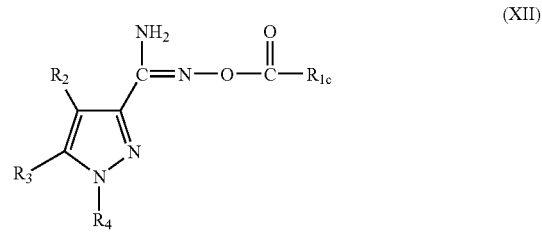

in which $R_{1c}$, $R_2$, $R_3$ and $R_4$ are as defined for a compound of formula (I), is cyclized.

The cyclization reaction is carried out generally in a solvent, such as n-butanol, at a temperature between ambient temperature and the reflux temperature of the solvent.

The compounds of formula (I) thus obtained can subsequently be separated from the reaction medium and purified according to conventional methods, for example by crystallization or chromatography.

The compounds of formula (II) are prepared by reaction of a compound of formula:

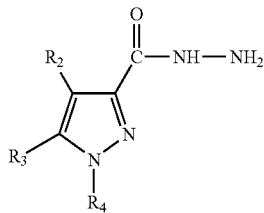

(III)

in which $R_2$, $R_3$ and $R_4$ are as defined for a compound of formula (I), with an acid or a functional derivative of this acid of formula:

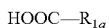 (VI)

HOOC—$R_{1a}$ in which $R_{1a}$ is as defined for a compound of formula (I), under the operating conditions as defined above for the reaction of a compound of formula (V).

The compounds of formula (III) are prepared from the compounds of formula:

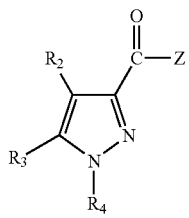

(VII)

in which $R_2$, $R_3$ and $R_4$ are as defined for a compound of formula (I) and Z represents a hydroxyl or a ($C_1$-$C_2$)alkoxy.

When Z=OH, the acid of formula (VII) itself or a functional derivative of this acid is reacted with a compound of formula:

H$_2$N—NH—Pg  (VIII)

in which Pg represents an N-protecting group, such as tert-butyloxycarbonyl, under the conditions described above for a compound of formula (V) and the intermediate compound obtained is deprotected according to conventional methods.

When Z=($C_1$-$C_2$)alkoxy, the ester of formula (VII) is reacted with hydrazine in a solvent, such as ethanol, and at a temperature between ambient temperature and the reflux temperature of the solvent.

The compounds of formula (IV) are available commercially or are described in the literature or else can be prepared according to methods which are described therein or which are known to a person skilled in the art, such as the reaction of phosgene with the corresponding amine.

The compounds of formulae (V) and (VI) are known.

The compounds of formula (VII) are known and are prepared according to known methods, such as those disclosed in EP 0 656 354, EP 0 576 357, WO 00/46209 and WO 2005/000820.

The compounds of formula (VIII), (IX) and (X) are commercially available or are described in the literature or else can be prepared according to methods which are described therein or which are known to a person skilled in the art.

The compounds of formula (XI) are prepared by reaction of an acid of formula (VII) (Z=OH) or of a functional derivative of this acid with a compound of formula:

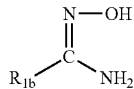

(XIII)

in which $R_{1b}$ is as defined for a compound of formula (I), under the operating conditions as defined above for the reaction of a compound of formula (V).

The compounds of formula (XII) are prepared by reaction of a compound of formula:

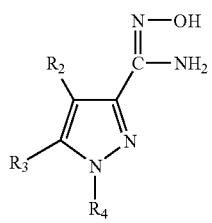

(XIV)

in which $R_2$, $R_3$, and $R_4$ are as defined for a compound of formula (I), with an acid or a functional derivative of this acid of formula:

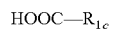

HOOC—$R_{1c}$  (XV)

in which $R_{1c}$ is as defined for a compound of formula (I), under the operating conditions as defined above for the reaction of a compound of formula (V).

The compounds of formula (XIII) are known or are prepared according to known methods, such as the reaction of hydroxylamine with a compound of formula $R_{1b}$CN (XVI) in a solvent, such as ethanol, and at the reflux temperature of the solvent.

The compounds of formula (XIV) are prepared by reaction of hydroxylamine with a compound of formula:

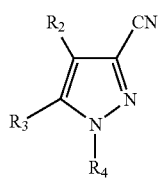

(XVII)

in which $R_2$, $R_3$ and $R_4$ are as defined for a compound of formula (I).

The compounds of formulae (XV) and (XVI) are known.

The compounds of formula (XVII) are prepared according to the processes disclosed in EP 0 576 357.

Another subject-matter of the invention, according to another of its aspects, is some novel compounds of formulae (II), (XI) and (XII). These compounds are of use as intermediates in the synthesis of the compounds of formula (I).

Thus, a subject-matter of the invention is compounds of formula:

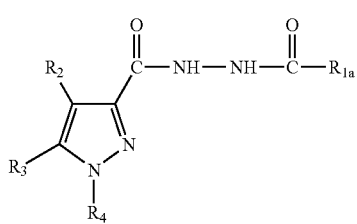
(II)

in which:
R$_{1a}$ represents:
- a (C$_1$-C$_7$)alkyl which is unsubstituted or substituted by:
  a) one or more halogen atoms;
  b) a (C$_1$-C$_4$)alkoxy or a phenoxy;
  c) a phenyl which is unsubstituted or mono-, di- or trisubstituted by substituents chosen independently from a halogen atom, a (C$_1$-C$_4$)alkyl, a (C$_1$-C$_4$)alkoxy, a trifluoromethyl radical or a trifluoromethoxy radical;
  d) an aromatic heterocyclic radical chosen from a thienyl, a pyrrolyl, an imidazolyl, a furyl or a pyrazolyl;
- a nonaromatic C$_3$-C$_{12}$ carbocyclic radical which is unsubstituted or substituted one or more times by a (C$_1$-C$_4$)alkyl;
- a phenyl which is unsubstituted or mono-, di- or trisubstituted by substituents chosen independently from a halogen atom, a (C$_1$-C$_4$)alkyl, a (C$_1$-C$_4$)alkoxy, a trifluoromethyl radical or a trifluoromethoxy radical;
- an —NR$_5$R$_6$ group;
- a —COOR$_9$ group;

R$_2$ represents a (C$_1$-C$_5$)alkyl or a cyano;

R$_3$ represents a phenyl which is unsubstituted or mono-, di- or trisubstituted by substituents chosen independently from a halogen atom, a (C$_1$-C$_4$)alkyl, a (C$_1$-C$_4$)alkoxy, a trifluoromethyl radical, a trifluoromethoxy radical or an S(O)$_n$Alk group;

R$_4$ represents a phenyl which is unsubstituted or mono-, di- or trisubstituted by substituents chosen independently from a halogen atom, a (C$_1$-C$_4$)alkyl, a (C$_1$-C$_4$)alkoxy, a trifluoromethyl radical, a trifluoromethoxy radical or an S(O)$_n$Alk group;

R$_5$ and R$_6$ each independently represent a hydrogen atom or a (C$_1$-C$_4$)alkyl;

or else R$_5$ and R$_6$, together with the nitrogen atom to which they are bonded, constitute a heterocyclic radical chosen from azetidine, pyrrolidine, piperidine or morpholine;

R$_9$ represents a (C$_1$-C$_4$)alkyl;

n represents 0, 1 or 2;

Alk represents a (C$_1$-C$_4$)alkyl.

Preference is particularly given to the compounds of formula (II) in which:
R$_2$ represents a methyl, an ethyl or a cyano;
R$_3$ represents a 4-bromophenyl or a 4-chlorophenyl;
R$_4$ represents a 2-chlorophenyl or a 2,4-dichlorophenyl.

Thus, a subject-matter of the invention is compounds of formula:

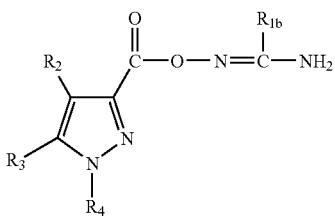
(XI)

in which:
R$_{1b}$ represents:
- a (C$_1$-C$_7$)alkyl which is unsubstituted or substituted by:
  a) one or more halogen atoms;
  b) a (C$_1$-C$_4$)alkoxy or a phenoxy;
  c) a phenyl which is unsubstituted or mono-, di- or trisubstituted by substituents chosen independently from a halogen atom, a (C$_1$-C$_4$)alkyl, a (C$_1$-C$_4$)alkoxy, a trifluoromethyl radical or a trifluoromethoxy radical;
  d) an aromatic heterocyclic radical chosen from a thienyl, a pyrrolyl, an imidazolyl, a furyl or a pyrazolyl;
- a nonaromatic C$_3$-C$_{12}$ carbocyclic radical which is unsubstituted or substituted one or more times by a (C$_1$-C$_4$)alkyl;
- a phenyl which is unsubstituted or mono-, di- or trisubstituted by substituents chosen independently from a halogen atom, a (C$_1$-C$_4$)alkyl, a (C$_1$-C$_4$)alkoxy, a trifluoromethyl radical or a trifluoromethoxy radical;
- an —NR$_{15}$R$_{16}$ group;

R$_2$ represents a (C$_1$-C$_5$)alkyl or a cyano;

R$_3$ represents a phenyl which is unsubstituted or mono-, di- or trisubstituted by substituents chosen independently from a halogen atom, a (C$_1$-C$_4$)alkyl, a (C$_1$-C$_4$)alkoxy, a trifluoromethyl radical, a trifluoromethoxy radical or an S(O)$_n$Alk group;

R$_4$ represents a phenyl which is unsubstituted or mono-, di- or trisubstituted by substituents chosen independently from a halogen atom, a (C$_1$-C$_4$)alkyl, a (C$_1$-C$_4$)alkoxy, a trifluoromethyl radical, a trifluoromethoxy radical or an S(O)$_n$Alk group;

R$_{15}$ and R$_{16}$ each independently represent a hydrogen atom or a (C$_1$-C$_4$)alkyl;

n represents 0, 1 or 2;

Alk represents a (C$_1$-C$_4$)alkyl.

Preference is particularly given to the compounds of formula (XI) in which:
R$_2$ represents a methyl;
R$_3$ represents a 4-chlorophenyl;
R$_4$ represents a 2,4-dichlorophenyl.

Thus, a subject-matter of the invention is compounds of formula:

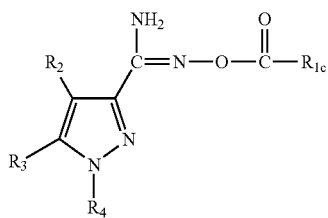

(XII)

in which:

$R_{1c}$ represents:
- a ($C_1$-$C_7$)alkyl which is unsubstituted or substituted by:
  a) one or more halogen atoms;
  b) a ($C_1$-$C_4$)alkoxy or a phenoxy;
  c) a phenyl which is unsubstituted or mono-, di- or trisubstituted by substituents chosen independently from a halogen atom, a ($C_1$-$C_4$)alkyl, a ($C_1$-$C_4$)alkoxy, a trifluoromethyl radical or a trifluoromethoxy radical;
  d) an aromatic heterocyclic radical chosen from a thienyl, a pyrrolyl, an imidazolyl, a furyl or a pyrazolyl;
- a nonaromatic $C_3$-$C_{12}$ carbocyclic radical which is unsubstituted or substituted one or more times by a ($C_1$-$C_4$)alkyl;
- a phenyl which is unsubstituted or mono-, di- or trisubstituted by substituents chosen independently from a halogen atom, a ($C_1$-$C_4$)alkyl, a ($C_1$-$C_4$)alkoxy, a trifluoromethyl radical or a trifluoromethoxy radical;
- an —$NR_{15}R_{16}$ group;

$R_2$ represents a ($C_1$-$C_5$)alkyl or a cyano;

$R_3$ represents a phenyl which is unsubstituted or mono-, di- or trisubstituted by substituents chosen independently from a halogen atom, a ($C_1$-$C_4$)alkyl, a ($C_1$-$C_4$)alkoxy, a trifluoromethyl radical, a trifluoromethoxy radical or an S(O)$_n$Alk group;

$R_4$ represents a phenyl which is unsubstituted or mono-, di- or trisubstituted by substituents chosen independently from a halogen atom, a ($C_1$-$C_4$)alkyl, a ($C_1$-$C_4$)alkoxy, a trifluoromethyl radical, a trifluoromethoxy radical or an S(O)$_n$Alk group;

$R_{15}$ and $R_{16}$ each independently represent a hydrogen atom or a ($C_1$-$C_4$)alkyl;

n represents 0, 1 or 2;

Alk represents a ($C_1$-$C_4$)alkyl.

Preference is particularly given to the compounds of formula (XII) in which:

$R_2$ represents a methyl;
$R_3$ represents a 4-chlorophenyl;
$R_4$ represents a 2,4-dichlorophenyl.

The following EXAMPLES describe the preparation of some compounds in accordance with the invention. These examples are not limiting and serve only to illustrate the present invention. The numbers of the compounds given in the examples refer to those shown in Tables 2, 3 and 4 below, in which the chemical structures and the physical properties of a few compounds according to the invention are illustrated.

The following abbreviations are used in the Preparations and in the Examples:

ether: diethyl ether
isopropyl ether: diisopropyl ether
EtOH: ethanol
MeOH: methanol
DMSO: dimethyl sulfoxide
DMF: N,N-dimethylformamide
THF: tetrahydrofuran
DCM: dichloromethane
AcOEt: ethyl acetate
DIPEA: diisopropylethylamine
TFA: trifluoroacetic acid
2N ethereal hydrochloric acid: 2N solution of hydrochloric acid in diethyl ether
PyBOP: (benzotriazol-1-yloxy)tris(pyrrolidino)phosphonium hexafluorophosphate
HOBT: 1-hydroxybenzotriazole
M.p.: melting point
AT: ambient temperature
B.p.: boiling point
HPLC: high performance liquid chromatography
Silica H: 60 H silica gel sold by Merck (Darmstadt)
pH=2 buffer solution: solution of 16.66 g of KHSO$_4$ and 32.32 g of K$_2$SO$_4$ in 1 liter of water.

The nuclear magnetic resonance spectra are recorded at 200 MHz in d$_6$-DMSO. Use is made of the following abbreviations in interpreting the spectra: s: singlet, d: doublet, t: triplet, q: quartet, qt: quintet, m: unresolved peak, mt: multiplet, bs: broad singlet, sd: split doublet, spt: septet.

The compounds according to the invention are analyzed by LC/UVAMS (liquid chromatography/UV detection/mass spectrometry) coupling. The molecular peak (MH$^+$) and the retention time (rt) in minutes are measured.

The equipment used, sold by Agilent, consists of an HP 1100 chromatograph equipped with an Agilent diode array detector and an MSD Quad quadrupole mass spectrometer.

Method:

Use is made of a Symmetry C 18 column of 2.1×50 mm, 3.5 μm, at 30° C., flow rate 0.4 ml/minute.

The eluent is composed as follows:

solvent A: 0.005% of trifluoroacetic acid (TFA) in water at pH 3.15;
solvent B: 0.005% of TFA in acetonitrile.

Gradient:

| Time (minutes) | % A | % B |
|---|---|---|
| 0 | 100 | 0 |
| 10 | 10 | 90 |
| 15 | 10 | 90 |
| 16 | 100 | 0 |
| 20 | 100 | 0 |

UV detection is carried out at λ=210 nM and mass detection is carried out in positive electrospray (ESI) mode, in order to observe the ions resulting from the protonation of the compounds analyzed (MH$^+$).

Preparations

1. Preparations of the Compounds of Formula (VII)

Preparation 1.1

Ethyl 1-(2-chlorophenyl)-5-(4-chlorophenyl)-4-methyl-1H-pyrazole-3-carboxylate

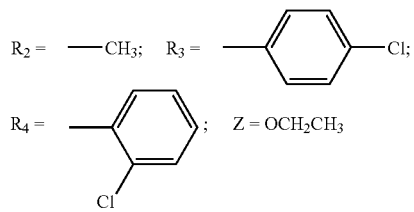

A) Lithium salt of ethyl 4-(4-chlorophenyl)-3-methyl-2-oxo-4-oxydobut-3-enoate

A solution of 125 ml of a 1M solution of the lithium salt of hexamethyldisilazane in THF and 500 ml of ether is cooled to −78° C. under a nitrogen atmosphere, a solution of 21 g of 4-chloropropiophenone in 100 ml of ether is added dropwise and the mixture is left stirring for 45 minutes. Subsequently 19.2 ml of diethyl oxalate are rapidly added and the mixture is left stirring for 16 hours while allowing the temperature to rise to AT. The precipitate formed is filtered off, washed with ether and dried under vacuum. 12.6 g of the expected compound are obtained.

B) Ethyl 1-(2-chlorophenyl)-5-(4-chlorophenyl)-4-methyl-1H-pyrazole-3-carboxylate 6.5 g of 2-chlorophenylhydrazine hydrochloride are added to a solution of 10 g of the compound obtained in the preceding stage in 100 ml of EtOH and the mixture is left stirring overnight at AT. The precipitate formed is filtered off, washed with EtOH and then with ether and dried under vacuum. The precipitate is taken up in 50 ml of acetic acid and heated at reflux for 4 hours. After cooling to AT, the reaction mixture is poured into 400 ml of ice-cold water and the precipitate formed is filtered off. 4 g of the expected compound are obtained.

Preparation 1.2

5-(4-Chlorophenyl)-1-(2,4-dichlorophenyl)-4-methyl-1H-pyrazole-3-carboxylic acid

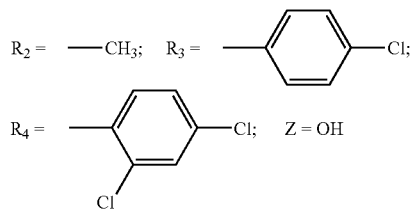

This compound is prepared according to the procedures disclosed in EP0656354 B.

Preparation 1.3

5-(4-Bromophenyl)-1-(2,4-dichlorophenyl)-4-ethyl-1H-pyrazole-3-carboxylic acid

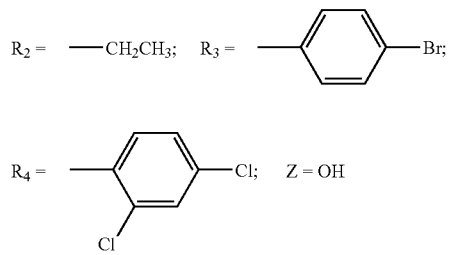

This compound is prepared according to the procedures disclosed in WO 00/46209.

Preparation 1.4

Ethyl 5-(4-chlorophenyl)-4-cyano-1-(2,4-dichlorophenyl)-1H-pyrazole-3-carboxylate

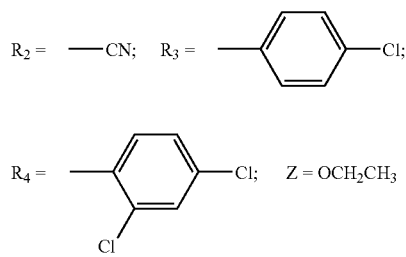

This compound is prepared according to the procedures disclosed in WO 2005/000820.

Preparation 1.5

Ethyl 5-(4-bromophenyl)-4-cyano-1-(2,4-dichlorophenyl)-1H-pyrazole-3-carboxylate

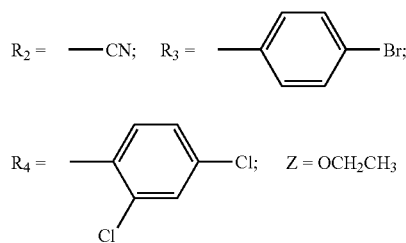

This compound is prepared according to the procedures disclosed in WO 2005/000820.

2. Preparations of the Compounds of Formula (III)

Preparation 2.1

1-(2-Chlorophenyl)-5-(4-chlorophenyl)-4-methyl-1H-pyrazole-3-carbohydrazide (III):

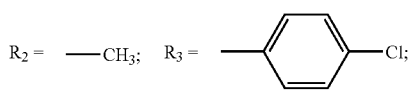

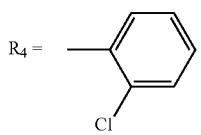

A mixture of 1 g of the compound obtained in Preparation 1.1 and 5 ml of hydrazine hydrate in 30 ml of ethanol is heated at reflux for 3 hours. The reaction mixture is concentrated under vacuum, the residue is taken up in water and extracted with ether, the organic phase is washed with water and dried over $MgSO_4$ and the solvent is evaporated under vacuum. The residue is taken up in isopropyl ether and the precipitate formed is filtered off. 0.79 g of the expected compound is obtained.

Preparation 2.2

5-(4-Chlorophenyl)-1-(2,4-dichlorophenyl)-4-methyl-1H-pyrazole-3-carbohydrazide (III):

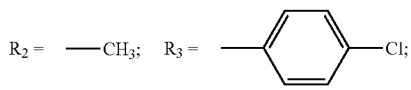

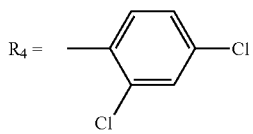

A) 5-(4-Chlorophenyl)-1-(2,4-dichlorophenyl)-4-methyl-1H-pyrazole-3-carbonyl chloride 2.9 ml of thionyl chloride are added to a suspension of 5 g of the compound obtained in Preparation 1.2 in 50 ml of 1,2-dichloroethane, the mixture is then heated at 60° C. for 2 hours and the reaction mixture is concentrated under vacuum. 5.25 g of the expected compound are obtained, which compound is used as is.

B) tert-Butyl 2-[[5-(4-chlorophenyl)-1-(2,4-dichlorophenyl)-4-methyl-1H-pyrazol-3-yl]carbonyl]hydrazinecarboxylate A mixture of 1.82 g of tert-butyl hydrazinecarboxylate and 2.4 ml of triethylamine in 50 ml of DCM is cooled to 0° C., a solution of 5.24 g of the compound obtained in stage A in 50 ml of DCM is added and the mixture is left stirring while allowing the temperature to rise to AT. The reaction mixture is washed with water, with a buffer solution at pH=2 and with a saturated $NaHCO_3$ solution, the organic phase is dried over $MgSO_4$ and the solvent is evaporated under vacuum. The residue is taken up in isopropyl ether, pentane is added and the precipitate formed is filtered off. 6.2 g of the expected compound are obtained.

C) 5-(4-Chlorophenyl)-1-(2,4-dichlorophenyl)-4-methyl-1H-pyrazole-3-carbohydrazide 20 ml of 2N ethereal hydrochloric acid are added to a solution of 6.2 g of the compound obtained in stage B in 100 ml of MeOH and then the mixture is heated at 40° C. for 3 hours. The reaction mixture is concentrated under vacuum, the residue is extracted with ether, the organic phase is washed twice with a 10% $NaHCO_3$ solution and dried over $MgSO_4$, and the solvent is evaporated under vacuum. The residue is taken up in pentane and the precipitate formed is filtered off. 4.09 g of the expected compound are obtained.

Preparation 2.3

5-(4-Bromophenyl)-1-(2,4-dichlorophenyl)-4-ethyl-1H-pyrazole-3-carbohydrazide (III):

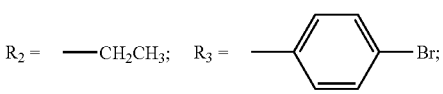

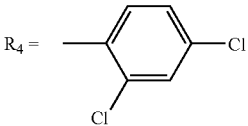

A) 5-(4-Bromophenyl)-1-(2,4-dichlorophenyl)-4-ethyl-1H-pyrazole-3-carbonyl chloride 5.6 ml of thionyl chloride are added to a mixture of 10 g of the compound obtained in Preparation 1.3 in 100 ml of 1,2-dichloroethane and then the mixture is heated at 80° C. for 2 hours. The reaction mixture is concentrated under vacuum and 10.5 g of the expected compound are obtained, which compound is used as is.

B) tert-Butyl 2-[[5-(4-bromophenyl)-1-(2,4-dichlorophenyl)-4-ethyl-1H-pyrazol-3-yl]carbonyl]hydrazinecarboxylate A mixture of 3.2 g of tert-butyl hydrazinecarboxylate and 3.9 ml of triethylamine in 100 ml of DCM is cooled to 0° C., a solution of 10.5 g of the compound obtained in stage A in 100 ml of DCM is added dropwise and the mixture is left stirring while allowing the temperature to rise to AT. The reaction mixture is washed with water, with a pH=2 buffer solution and with a saturated $NaHCO_3$ solution, the organic phase is dried over $MgSO_4$ and the solvent is evaporated under vacuum. 12.7 g of the expected compound are obtained.

C) 5-(4-Bromophenyl)-1-(2,4-dichlorophenyl)-4-ethyl-1H-pyrazole-3-carbohydrazide 40 ml of 2N ethereal hydrochloric acid are added to a solution of 12.7 g of the compound obtained in stage B in 200 ml of MeOH and the mixture is then heated at 40° C. for 3 hours. The reaction mixture is concentrated under vacuum, the residue is extracted with ether, the organic phase is washed twice with a 10% NaHCO$_3$ solution and dried over MgSO$_4$, and the solvent is evaporated under vacuum. 8.3 g of the expected compound are obtained after crystallization from an ether/pentane mixture.

Preparation 2.4

5-(4-Chlorophenyl)-4-cyano-1-(2,4-dichlorophenyl)-1H-pyrazole-3-carbohydrazide

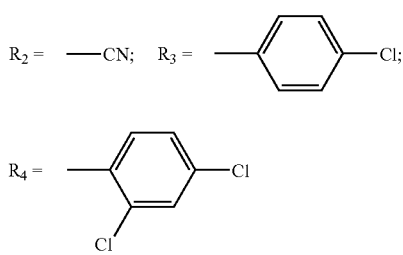

A mixture of 6.5 g of the compound obtained in Preparation 1.4 and 35 ml of hydrazine hydrate in 200 ml of EtOH is heated to 60° C. and is then left stirring while allowing the temperature to return to AT. The reaction mixture is concentrated under vacuum, the residue is taken up in a water/ether mixture and the precipitate formed is filtered off and washed with water and then with ether. 5.3 g of the expected compound are obtained after drying under vacuum at 60° C.

Preparation 2.5

5-(4-Bromophenyl)-4-cyano-1-(2,4-dichlorophenyl)-1H-pyrazole-3-carbohydrazide

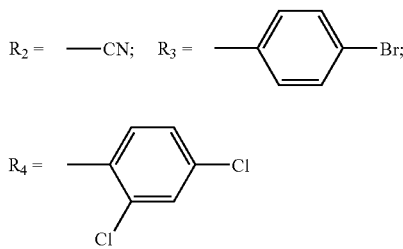

A mixture of 4.9 g of the compound obtained in Preparation 1.5 and 25 ml of hydrazine hydrate in 150 ml of EtOH is heated to 60° C. and then left stirring while allowing the temperature to return to AT. The crystalline product formed is filtered off and washed with EtOH and then with isopropyl ether. 2.99 g of the expected compound are obtained.

3. Preparations of the Compounds of Formula (II)

Preparation 3.1

1-(2-Chlorophenyl)-5-(4-chlorophenyl)-N'-(2,2-dimethylpropanoyl)-4-methyl-1H-pyrazole-3-carbohydrazide 0.16 ml of pivaloyl chloride is added, at AT, to a solution of 0.4 g of the compound obtained in Preparation 2.1 and 0.23 ml of triethylamine in 10 ml of DCM and the mixture is left stirring for 30 minutes. The reaction mixture is washed with water, with a 1N HCl solution and with a saturated NaHCO$_3$ solution, the organic phase is dried over MgSO$_4$ and the solvent is evaporated under vacuum. The residue is taken up in isopropyl ether and the precipitate formed is filtered off. 0.43 g of the expected compound is obtained.

Preparation 3.3

5-(4-Chlorophenyl)-1-(2,4-dichlorophenyl)-N'-(2,2-dimethylpropanoyl)-4-methyl-1H-pyrazole-3-carbohydrazide A solution of 0.7 g of the compound obtained in Preparation 2.2 and 0.3 ml of triethylamine in 15 ml of DCM is cooled to 0° C., 0.22 ml of pivaloyl chloride is added and the mixture is left stirring while allowing the temperature to rise to AT. The reaction mixture is washed with water and with a saturated NaHCO$_3$ solution, the organic phase is dried over MgSO$_4$ and the solvent is evaporated under vacuum. The residue is taken up in isopropyl ether and the crystalline product formed is filtered off and washed with isopropyl ether and then with pentane. 0.77 g of the expected compound is obtained.

Preparation 3.5

5-(4-Chlorophenyl)-1-(2,4-dichlorophenyl)-4-methyl-N'-(3-methylbutanoyl)-1H-pyrazole-3-carbohydrazide A mixture of 0.5 g of the compound obtained in Preparation 2.2, 0.13 g of isovaleric acid, 0.35 ml of triethylamine and 0.79 g of PyBOP in 10 ml of DCM is left stirring overnight at AT. The reaction mixture is concentrated under vacuum, the residue is extracted with ether, the organic phase is washed with water, with a 1N HCl solution and with a 10% NaHCO$_3$ solution and dried over MgSO$_4$, and the solvent is evaporated under vacuum. 0.52 g of the expected compound is obtained after crystallization from isopropyl ether.

Preparation 3.7

5-(4-Chlorophenyl)-1-(2,4-dichlorophenyl)-4-methyl-N'-(4-phenylbutanoyl)-1H-pyrazole-3-carbohydrazide A mixture of 0.64 g of the compound obtained in Preparation 2.2, 0.27 g of 4-phenylbutyric acid, 0.56 ml of triethylamine and 1.01 g of PyBOP in 10 ml of DCM is left stirring overnight at AT. The reaction mixture is concentrated under vacuum, the residue is extracted with ether, the organic phase is washed with water, with a 1N HCl solution, with water and with a 10% NaHCO$_3$ solution and dried over MgSO$_4$, and the solvent is evaporated under vacuum. 0.76 g of the expected compound is obtained after crystallization from isopropyl ether.

Preparation 3.11

N'-Acetyl-5-(4-bromophenyl)-1-(2,4-dichlorophenyl)-4-ethyl-1H-pyrazole-3-carbohydrazide A solution of 0.8 g of the compound obtained in Preparation 2.3 and 0.29 ml of triethylamine in 15 ml of DCM is cooled to 0° C., 0.13 ml of acetyl chloride is added and the mixture is left stirring while allowing the temperature to rise to AT. The reaction mixture is washed with water and with a 10% NaHCO$_3$ solution, the organic phase is dried over MgSO$_4$ and the solvent is evaporated under vacuum. 0.85 g of the expected compound is obtained.

Preparation 3.14

5-(4-Bromophenyl)-1-(2,4-dichlorophenyl)-4-ethyl-N'-(2-propylpentanoyl)-1H-pyrazole-3-carbohydrazide A mixture of 0.7 g of the compound obtained in Preparation 2.3, 0.23 g of 2-propylpentanoic acid, 0.54 ml of triethylamine and 0.96 g of PyBOP in 20 ml of DCM is left stirring overnight at AT. The reaction mixture is concentrated under vacuum, the residue is extracted with ether, the organic phase is washed with water, with a 1N HCl solution, with water and with a 10% NaHCO$_3$ solution and dried over MgSO$_4$, and the solvent is evaporated under vacuum. The residue is chromatographed on silica gel, elution being carried out with heptane and then with a heptane/AcOEt (80/20; v/v) mixture. 0.88 g of the expected compound is obtained, which compound is crystallized from an isopropyl ether/pentane mixture.

Preparation 3.21

N'-Butyryl-5-(4-chlorophenyl)-4-cyano-1-(2,4-dichlorophenyl)-1H-pyrazole-3-carbohydrazide A mixture of 0.5 g of the compound obtained in Preparation 2.4 and 0.31 ml of triethylamine in 10 ml of DCM is cooled to 0° C., 0.19 ml of butyryl chloride is added and the mixture is left stirring for 45 minutes. The reaction mixture is washed with water, with a 1N HCl solution and with a 10% NaHCO$_3$ solution, the organic phase is dried over MgSO$_4$ and the solvent is evaporated under vacuum. 0.55 g of the expected compound is obtained.

Preparation 3.24

5-(4-Chlorophenyl)-4-cyano-1-(2,4-dichlorophenyl)-N'-(4-phenylbutanoyl)-1H-pyrazole-3-carbohydrazide A mixture of 0.5 g of the compound obtained in Preparation 2.4, 0.21 g of 4-phenylbutyric acid, 0.43 ml of triethylamine and 0.76 g of PyBOP in 15 ml of DCM is left stirring overnight at AT. The reaction mixture is concentrated under vacuum, the residue is taken up in a water/ether mixture and the crystalline product formed is filtered off and washed with water and then with ether. 0.54 g of the expected compound is obtained after drying under vacuum.

Preparation 3.26

5-(4-Bromophenyl)-4-cyano-1-(2,4-dichlorophenyl)-N'-isobutyryl-1H-pyrazole-3-carbohydrazide 0.19 ml of isobutyryl chloride is added, dropwise and at AT, to a solution of 0.5 g of the compound obtained in Preparation 2.5 and 0.23 ml of triethylamine in 15 ml of DCM. The reaction mixture is washed with water, with a 1N HCl solution and with a 10% NaHCO$_3$ solution, the organic phase is dried over MgSO$_4$ and the solvent is evaporated under vacuum. 0.55 g of the expected compound is obtained.

Preparation 3.28

5-(4-Bromophenyl)-4-cyano-1-(2,4-dichlorophenyl)-N'-(4-phenylbutanoyl)-1H-pyrazole-3-carbohydrazide A mixture of 0.5 g of the compound obtained in Preparation 2.5, 0.19 g of 4-phenylbutyric acid, 0.32 ml of triethylamine and 0.7 g of PyBOP in 15 ml of DCM is left stirring overnight at AT. The reaction mixture is concentrated under vacuum to half its volume and the crystalline product formed is filtered off and washed with DCM and then with ether. 0.46 g of the expected product is obtained.

Preparation 3.39

Ethyl[2-[[5-(4-chlorophenyl)-1-(2,4-dichlorophenyl)-4-methyl-1H-pyrazol-3-yl]carbonyl]hydrazino]oxo)acetate A mixture of 10 g of the compound obtained in Preparation 2.2 and 2.2 ml of triethylamine in 100 ml of DCM is cooled to −20° C., 3.1 ml of ethoxalyl chloride are added dropwise and the mixture is left stirring while allowing the temperature to rise to AT. The reaction mixture is extracted with DCM, the organic phase is washed with water and dried over MgSO$_4$, and the solvent is evaporated under vacuum. 12.5 g of the expected compound are obtained.

Preparation 3.42

Ethyl[2-[[5-(4-bromophenyl)-1-(2,4-dichlorophenyl)-4-ethyl-1H-pyrazol-3-yl]carbonyl]hydrazino](oxo)acetate A mixture of 3 g of the compound obtained in Preparation 2.3 and 1.1 ml of triethylamine in 50 ml of DCM is cooled to −20° C., 0.81 ml of ethoxalyl chloride is added dropwise and the mixture is left stirring while allowing the temperature to rise to AT.

The reaction mixture is extracted with DCM, the organic phase is washed with water and dried over MgSO$_4$, and the solvent is evaporated under vacuum. 3.7 g of the expected compound are obtained.

The compounds of formula (TI) collated in Table 1 below are prepared by following the procedures described in Preparations 3 above.

TABLE 1
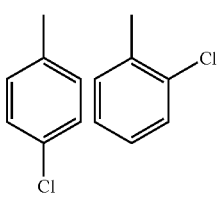
(II)
| Preparation | R₁ | R₂ | R₃ | R₄ |
|---|---|---|---|---|
| 3.1 | —C(CH₃)₃ | —CH₃ | 4-Cl-C₆H₄ | 2-Cl-C₆H₄ |
| 3.2 (a) | —CH(CH₃)₂ | —CH₃ | 4-Cl-C₆H₄ | 2-Cl-C₆H₄ |
| 3.3 | —C(CH₃)₃ | —CH₃ | 4-Cl-C₆H₄ | 2,4-Cl₂-C₆H₃ |
| 3.4 (b) | —CH(CH₃)₂ | —CH₃ | 4-Cl-C₆H₄ | 2,4-Cl₂-C₆H₃ |
| 3.5 | —CH₂CH(CH₃)₂ | —CH₃ | 4-Cl-C₆H₄ | 2,4-Cl₂-C₆H₃ |
| 3.6 (c) | —CH(CH₂CH₃)₂ | —CH₃ | 4-Cl-C₆H₄ | 2,4-Cl₂-C₆H₃ |

TABLE 1-continued
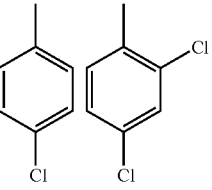
| Preparation | R₁ | R₂ | R₃ | R₄ |
|---|---|---|---|---|
| 3.7 | —CH₂CH₂CH₂—C₆H₅ | —CH₃ | 4-Cl-C₆H₄ | 2,4-Cl₂-C₆H₃ |
| 3.8 (b) | cyclohexyl | —CH₃ | 4-Cl-C₆H₄ | 2,4-Cl₂-C₆H₃ |
| 3.9 (b) | 1-adamantyl | —CH₃ | 4-Cl-C₆H₄ | 2,4-Cl₂-C₆H₃ |
| 3.10 (b) | piperidin-1-yl | —CH₃ | 4-Cl-C₆H₄ | 2,4-Cl₂-C₆H₃ |
| 3.11 | —CH₃ | —CH₂CH₃ | 4-Br-C₆H₄ | 2,4-Cl₂-C₆H₃ |
| 3.12 (d) | —CH(CH₃)₂ | —CH₂CH₃ | 4-Br-C₆H₄ | 2,4-Cl₂-C₆H₃ |

TABLE 1-continued
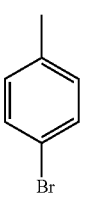
(II)
| Preparation | R₁ | R₂ | R₃ | R₄ |
|---|---|---|---|---|
| 3.13 (d) | —C(CH₃)₃ | —CH₂CH₃ | 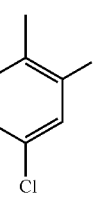 | 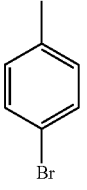 |
| 3.14 | —CH(CH₂CH₂CH₃)₂ | —CH₂CH₃ | 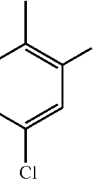 | 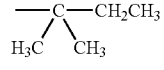 |
| 3.15 (e) | 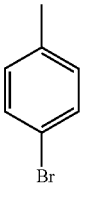 | —CH₂CH₃ | 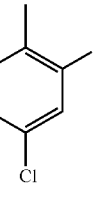 | 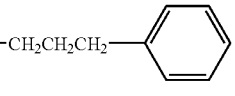 |
| 3.16 (e) | —CH₂CH₂CH₂— 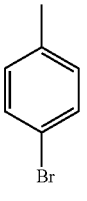 | —CH₂CH₃ | 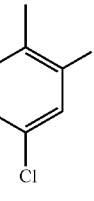 | 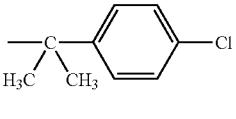 |
| 3.17 (e) | 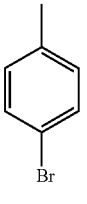 | —CH₂CH₃ | 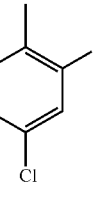 |  |
| 3.18 (d) | 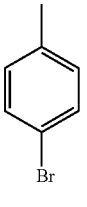 | —CH₂CH₃ | 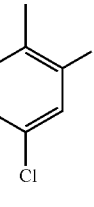 | |

TABLE 1-continued (II) Structure: R₂, R₃ on pyrazole ring with R₄ on N, connected via C(=O)—NH—NH—C(=O)—R₁

| Preparation | R₁ | R₂ | R₃ | R₄ |
|---|---|---|---|---|
| 3.19 (e) | cyclobutyl-CH₂- | —CH₂CH₃ | 4-Br-phenyl | 2,4-diCl-phenyl |
| 3.20 (d) | 3-CF₃-phenyl | —CH₂CH₃ | 4-Br-phenyl | 2,4-diCl-phenyl |
| 3.21 | —CH₂CH₂CH₃ | —CN | 4-Cl-phenyl | 2,4-diCl-phenyl |
| 3.22 (f) | —CH(CH₃)₂ | —CN | 4-Cl-phenyl | 2,4-diCl-phenyl |
| 3.23 (f) | —C(CH₃)₃ | —CN | 4-Cl-phenyl | 2,4-diCl-phenyl |
| 3.24 | —CH₂CH₂CH₂-phenyl | —CN | 4-Cl-phenyl | 2,4-diCl-phenyl |

TABLE 1-continued
(II)
| Preparation | R₁ | R₂ | R₃ | R₄ |
|---|---|---|---|---|
| 3.25 (f) | 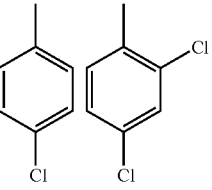 | —CN | 4-Cl-C₆H₄ | 2,4-Cl₂-C₆H₃ |
| 3.26 | —CH(CH₃)₂ | —CN | 4-Br-C₆H₄ | 2,4-Cl₂-C₆H₃ |
| 3.27 (g) | —C(CH₃)₃ | —CN | 4-Br-C₆H₄ | 2,4-Cl₂-C₆H₃ |
| 3.28 | —CH₂CH₂CH₂-C₆H₅ | —CN | 4-Br-C₆H₄ | 2,4-Cl₂-C₆H₃ |
| 3.29 (b) | —CH₂-C₆H₅ | —CH₃ | 4-Cl-C₆H₄ | 2,4-Cl₂-C₆H₃ |
| 3.30 (c) | —CH₂CH₂-C₆H₅ | —CH₃ | 4-Cl-C₆H₄ | 2,4-Cl₂-C₆H₃ |

TABLE 1-continued
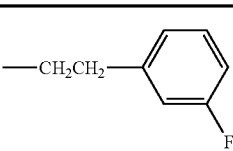
(II)
| Preparation | R₁ | R₂ | R₃ | R₄ |
|---|---|---|---|---|
| 3.31 (c) | 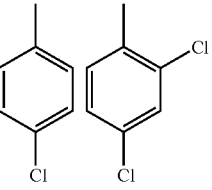 —CH₂CH₂—(3-F-phenyl) | —CH₃ | 4-Cl-phenyl | 2,4-di-Cl-phenyl |
| 3.32 (c) | 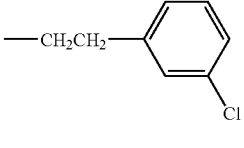 —CH₂CH₂—(3-Cl-phenyl) | —CH₃ | 4-Cl-phenyl | 2,4-di-Cl-phenyl |
| 3.33 (c) | 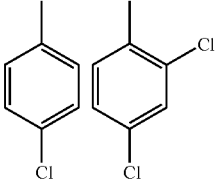 —CH₂CH₂CH₂—(4-OMe-phenyl) | —CH₃ | 4-Cl-phenyl | 2,4-di-Cl-phenyl |
| 3.34 (c) | 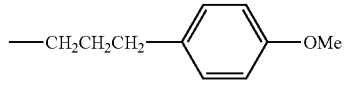 —CH₂CH₂CH₂CH₂—phenyl | —CH₃ | 4-Cl-phenyl | 2,4-di-Cl-phenyl |
| 3.35 (c) | 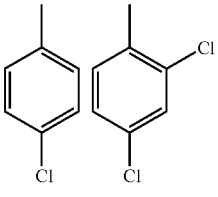 —CH₂CH₂—O—phenyl | —CH₃ | 4-Cl-phenyl | 2,4-di-Cl-phenyl |
| 3.36 (c) | 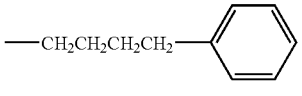 —CH₂-(2-thienyl) | —CH₃ | 4-Cl-phenyl | 2,4-di-Cl-phenyl |

TABLE 1-continued
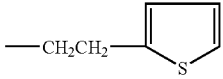
(II)
| Preparation | R₁ | R₂ | R₃ | R₄ |
|---|---|---|---|---|
| 3.37 (c) |  —CH₂CH₂— (2-thienyl) | —CH₃ |  4-Cl-phenyl |  2,4-diCl-phenyl |
| 3.38 (c) | 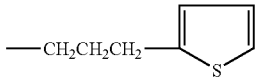 —CH₂CH₂CH₂— (2-thienyl) | —CH₃ |  4-Cl-phenyl |  2,4-diCl-phenyl |
| 3.39 | —COOCH₂CH₃ | —CH₃ |  4-Cl-phenyl | 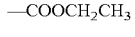 2,4-diCl-phenyl |
| 3.40 (e) | —CH₂CH₂— phenyl  | —CH₂CH₃ |  4-Br-phenyl |  2,4-diCl-phenyl |
| 3.41 (e) | 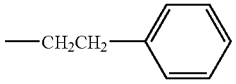 —CH₂CH₂— (2-thienyl) | —CH₂CH₃ |  4-Br-phenyl |  2,4-diCl-phenyl |
| 3.42 | —COOCH₂CH₃ | —CH₂CH₃ |  4-Br-phenyl | 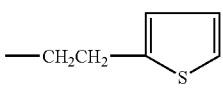 2,4-diCl-phenyl |

TABLE 1-continued

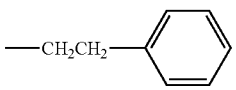

(II)

| Preparation | R₁ | R₂ | R₃ | R₄ |
|---|---|---|---|---|
| 3.43 (h) | —CH₂CH₂— | —CN | 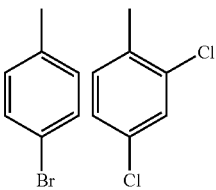 |  |

(a) Compound prepared according to the procedure described in Preparation 3.1 from the compound obtained in Preparation 2.1 and from the corresponding acid chlorides.
(b) Compound prepared according to the procedure described in Preparation 3.3 from the compound obtained in Preparation 2.2 and from the corresponding acid chlorides.
(c) Compound prepared according to the procedure described in Preparation 3.5 from the compound obtained in Preparation 2.2 and from the corresponding acids.
(d) Compound prepared according to the procedure described in Preparation 3.11 from the compound obtained in Preparation 2.3 and from the corresponding acid chlorides.
(e) Compound prepared according to the procedure described in Preparation 3.14 from the compound obtained in Preparation 2.3 and from the corresponding acids.
(f) Compound prepared according to the procedure described in Preparation 3.21 from the compound obtained in Preparation 2.4 and from the corresponding acid chlorides.
(g) Compound prepared according to the procedure described in Preparation 3.26 from the compound obtained in Preparation 2.5 and from the corresponding acid chlorides.
(h) Compound prepared according to the procedure described in Preparation 3.28 from the compound obtained in Preparation 2.5 and from the corresponding acids.

4. Preparations of the Compounds of Formula (XIII)

Preparation 4.1

N'-Hydroxy-2,2-dimethylpropanimidamide

A mixture of 5 g of pivalonitrile, 12 ml of a 50% solution of hydroxylamine in water and 50 ml of ethanol is heated at reflux for 48 hours. The reaction mixture is concentrated under vacuum, the residue is taken up in toluene and the solvent is evaporated under vacuum. The residue is taken up in pentane and the precipitate formed is filtered off. 6.16 g of the expected compound are obtained.

5. Preparations of the Compounds of Formula (XI)

Preparation 5.1

N'-[[[5-(4-Chlorophenyl)-1-(2,4-dichlorophenyl)-4-methyl-1H-pyrazol-3-yl]carbonyl]oxy]-2-methylpropanimidamide A mixture of 0.282 g of N'-hydroxy-2-methylpropanimidamide and 0.44 ml of triethylamine in 10 ml of DCM is cooled to 0° C., a solution of 1.05 g of the compound from Preparation 2.2, stage A, in 10 ml of DCM is added dropwise and the mixture is left stirring at AT for 1 hour. The reaction mixture is washed with water, the organic phase is dried over MgSO₄ and the solvent is evaporated under vacuum. The residue is taken up in DCM, isopropyl ether is added and the precipitate formed is filtered off. 1.15 g of the expected compound are obtained.

Preparation 5.2

N'-[[[5-(4-Chlorophenyl)-1-(2,4-dichlorophenyl)-4-methyl-1H-pyrazol-3-yl]carbonyl]oxy]-2,2-dimethylpropanimidamide A mixture of 0.32 g of the compound from Preparation 4.1 and 0.44 ml of triethylamine in 10 ml of DCM is cooled to 0° C., a solution of 1.05 g of the compound from Preparation 2.2, stage A, in 10 ml of DCM is added dropwise and the mixture is left stirring at AT for 2 hours. The reaction mixture is washed with water, the organic phase is dried over MgSO₄ and the solvent is evaporated under vacuum. The residue is taken up in isopropyl ether and the precipitate formed is filtered off. 1.19 g of the expected compound are obtained.

6. Preparations of the Compounds of Formula (XIV)

Preparation 6.1

5-(4-Chlorophenyl)-1-(2,4-dichlorophenyl)-N'-hydroxy-4-methyl-1H-pyrazole-3-carboximidamide A) 5-(4-Chlorophenyl)-1-(2,4-dichlorophenyl)-4-methyl-1H-pyrazole-3-carboxamide A mixture of 10 g of the compound from Preparation 1.2 and 5 ml of SOCl₂ in 100 ml of 1,2-dichloroethane is heated at 60° C. for 1 hour and then the reaction mixture is concentrated under vacuum. The acid chloride thus obtained is taken up in 100 ml of DCM, this solution is added dropwise to 40 ml of a 2M solution of ammonia in MeOH cooled beforehand to −10° C. and the mixture is left stirring overnight while allowing the temperature to rise to AT. The reaction mixture is concentrated under vacuum, the residue is extracted with AcOEt, the organic phase is washed with water and dried over $MgSO_4$, the solvent is evaporated under vacuum down to a volume of 50 ml, and the precipitate formed is filtered off and washed with isopropyl ether. 9 g of the expected compound are obtained.

B) 5-(4-Chlorophenyl)-1-(2,4-dichlorophenyl)-4-methyl-1H-pyrazole-3-carbonitrile 2.25 ml of trifluoroacetic anhydride are added to a mixture of 5 g of the compound from the preceding stage and 2.2 ml of pyridine in 100 ml of THF and the mixture is left stirring at AT for 20 minutes. 5 ml of water are added, the reaction mixture is concentrated under vacuum, the residue is extracted with ether, the organic phase is washed with water, with a 1N HCl solution and with a 10% $NaHCO_3$ solution and dried over $MgSO_4$, and the solvent is evaporated under vacuum. The residue is chromatographed on silica gel, elution being carried out with heptane and then with the gradient of the heptane/AcOEt mixture as far as (80/20: v/v). 3.25 g of the expected compound are obtained after crystallization from pentane.

C) 5-(4-Chlorophenyl)-1-(2,4-dichlorophenyl)-N'-hydroxy-4-methyl-1H-pyrazole-3-carboximidamide A mixture of 1 g of the compound from the preceding stage, 0.52 ml of a 50% solution of hydroxylamine in water and 10 ml of ethanol is heated at reflux for 5 minutes. After cooling to AT, the crystalline product formed is filtered off and washed with ethanol and then with pentane. 0.997 g of the expected compound is obtained.

7. Preparations of the Compounds of Formula (XII)

Preparation 7.1

5-(4-Chlorophenyl)-1-(2,4-dichlorophenyl)-N'-[(2,2-dimethylpropanoyl)oxy]-4-methyl-1H-pyrazole-3-carboximidamide 0.16 ml of 2,2-dimethylpropanoyl chloride is added dropwise to a mixture of 0.5 g of the compound from Preparation 6.1 and 0.21 ml of triethylamine in 10 ml of DCM and the mixture is left stirring at AT for 30 minutes. The reaction mixture is washed with water, the organic phase is dried over $MgSO_4$ and the solvent is evaporated under vacuum. The residue is taken up in isopropyl ether, pentane is added and the precipitate formed is filtered off. 0.56 g of the expected compound is obtained.

Preparation 7.2

5-(4-Chlorophenyl)-1-(2,4-dichlorophenyl)-4-methyl-N'-[(3-phenylpropanoyl)oxy]-1H-pyrazole-3-carboximidamide 0.19 ml of 3-phenylpropanoyl chloride is added dropwise to a mixture of 0.48 g of the compound from Preparation 6.1 and 0.2 ml of triethylamine in 10 ml of DCM and the mixture is left stirring at AT for 30 minutes. The reaction mixture is washed with water, the organic phase is dried over $MgSO_4$ and the solvent is evaporated under vacuum. 0.64 g of the expected compound is obtained.

Preparation 7.3

5-(4-Chlorophenyl)-1-(2,4-dichlorophenyl)-4-methyl-N'-[[3-(2-thienyl)propanoyl]oxy]-1H-pyrazole-3-carboximidamide 0.168 g of HOBT and then 0.19 ml of N,N'-diisopropylcarbodiimide are added to a mixture of 0.4 g of the compound from Preparation 6.1 and 0.158 g of 3-(2-thienyl)propanoic acid in 10 ml of DCM and the mixture is left stirring at AT overnight. The reaction mixture is concentrated under vacuum, the residue is extracted with ether, the organic phase is washed with a 10% $NaHCO_3$ solution, with water and with a 0.5M $KHSO_4$ solution and dried over $MgSO_4$, and the solvent is evaporated under vacuum. 0.53 g of the expected compound is obtained.

EXAMPLE 1

Compound No. 1

2-tert-Butyl-5-[1-(2-chlorophenyl)-5-(4-chlorophenyl)-4-methyl-1H-pyrazol-3-yl]-1,3,4-oxadiazole A mixture of 0.43 g of the compound obtained in Preparation 3.1 and 0.07 g of 4-toluenesulphonic acid monohydrate in 10 ml of toluene is heated at reflux overnight while removing the water formed using a Dean and Stark apparatus. Ether is added to the reaction mixture, the organic phase is washed with a saturated $NaHCO_3$ solution, the crystalline product formed is filtered off and washed with water and then with ether. After separating by settling the filtration mother liquor, the organic phase is dried over $MgSO_4$ and the solvent is evaporated under vacuum. The residue and the crystalline product isolated above are chromatographed on silica gel, elution being carried out with heptane and then with the gradient of the heptane/AcOEt mixture as far as (70/30; v/v). The product obtained is taken up in isopropyl ether and the precipitate formed is filtered off. 0.29 g of the expected compound is obtained.

EXAMPLE 2

Compound No. 3

2-tert-Butyl-5-[5-(4-chlorophenyl)-1-(2,4-dichlorophenyl)-4-methyl-1H-pyrazol-3-yl]-1,3,4-oxadiazole A mixture of 0.5 g of the compound obtained in Preparation 3.3 and 0.06 g of 4-toluenesulphonic acid monohydrate in 15 ml of toluene is heated at reflux for 18 hours while removing the water formed using a Dean and Stark apparatus. The reaction mixture is washed with a 10% $NaHCO_3$ solution, the organic phase is dried over $MgSO_4$ and the solvent is evaporated under vacuum. The residue is chromatographed on silica gel, elution being carried out with heptane and then with the gradient of the heptane/AcOEt mixture as far as (85/15; v/v). 0.31 g of the expected compound is obtained after crystallization from pentane.

EXAMPLE 3

Compound No. 10

1-[5-[5-(4-Chlorophenyl)-1-(2,4-dichlorophenyl)-4-methyl-1H-pyrazol-3-yl]-1,3,4-oxadiazol-2-yl]piperidine A mixture of 0.42 g of the compound obtained in Preparation 3.10, 0.16 g of 4-toluenesulphonyl chloride and 1.2 ml of triethylamine in 10 ml of DCM is left stirring under a nitrogen atmosphere for 5 days. The reaction mixture is washed with water, the organic phase is dried over $MgSO_4$ and the solvent is evaporated under vacuum. The residue is chromatographed on silica gel, elution being carried out with heptane and then with the gradient of the heptane/AcOEt mixture as far as (60/40; v/v). 0.21 g of the expected compound is obtained after crystallization from an isopropyl ether/pentane mixture.

EXAMPLE 4

Compound No. 11

5-[5-(4-Chlorophenyl)-1-(2,4-dichlorophenyl)-4-methyl-1H-pyrazol-3-yl]-1,3,4-oxadiazol-2-amine A mixture of 2.3 g of the compound obtained in Preparation 2.2 and 0.62 g of cyanogen bromide in 20 ml of ethanol is heated at reflux for 3 hours. 30 ml of water are subsequently added to the reaction mixture, followed by 0.52 g of $NaHCO_3$, and the precipitate formed is filtered off and washed with water and then with ether. 1.4 g of the expected compound are obtained after crystallization from ethanol.

EXAMPLE 5

Compound No. 12

N-[5-[5-(4-Chlorophenyl)-1-(2,4-dichlorophenyl)-4-methyl-1H-pyrazol-3-yl]-1,3,4-oxadiazol-2-yl]acetamide 0.42 ml of acetic anhydride is added to a mixture of 0.4 g of the compound No. 11 in 4 ml of pyridine and then the mixture is heated at 60° C. for 3 hours. The reaction mixture is poured into a water/1N HCl mixture and the precipitate formed is filtered off and washed with water. The precipitate is taken up in ether and the crystalline product formed is filtered off. 0.13 g of the expected compound is obtained.

EXAMPLE 6

Compound No. 13

N-[5-[5-(4-Chlorophenyl)-1-(2,4-dichlorophenyl)-4-methyl-1H-pyrazol-3-yl]-1,3,4-oxadiazol-2-yl]-2,2-dimethylpropanamide 0.5 ml of pivalic anhydride is added to a mixture of 0.4 g of the compound No. 11 in 4 ml of pyridine and then the mixture is heated at 60° C. for 3 hours. 0.5 ml of pivalic anhydride is subsequently added again and the mixture is heated at 120° C. overnight. The reaction mixture is poured onto ice, acidified to pH=1 by addition of a concentrated HCl solution and extracted with ether, the crystalline product formed is filtered off and is washed with water and then with ether. The crystalline product is dissolved in DCM, the organic phase is dried over $MgSO_4$ and the solvent is evaporated under vacuum. 0.37 g of the expected compound is obtained after crystallization from isopropyl ether.

EXAMPLE 7

Compound No. 14

2-[5-(4-Bromophenyl)-1-(2,4-dichlorophenyl)-4-ethyl-1H-pyrazol-3-yl]-5-methyl-1,3,4-oxadiazole A mixture of 0.85 g of the compound obtained in Preparation 3.11 and 0.07 g of 4-toluenesulphonic acid monohydrate in 20 ml of toluene is heated at reflux overnight while removing the water formed using a Dean and Stark apparatus. After cooling to AT, the reaction mixture is washed with a 10% $NaHCO_3$ solution, the organic phase is dried over $MgSO_4$ and the solvent is evaporated under vacuum. The residue is chromatographed on silica gel, elution being carried out with heptane and then with the heptane/AcOEt (75/25; v/v) mixture. 0.265 g of the expected compound is obtained after crystallization from isopropyl ether and then recrystallization from an EtOH/pentane mixture.

EXAMPLE 8

Compound No. 24

5-[5-(4-Bromophenyl)-1-(2,4-dichlorophenyl)-4-ethyl-1H-pyrazol-3-yl]-N,N-dimethyl-1,3,4-oxadiazol-2-amine A solution of 0.25 g of dichloromethylenedimethylammonium chloride in 10 ml of DCM is cooled to −20° C. under a nitrogen atmosphere, 0.5 g of the compound obtained in Preparation 2.3 is added, the mixture is left stirring for 10 minutes, 1 ml of triethylamine is then added and the mixture is left stirring overnight while allowing the temperature to rise to AT. The reaction mixture is washed with water and with a 10% $NaHCO_3$ solution, the organic phase is dried over $MgSO_4$ and the solvent is evaporated under vacuum. The residue is chromatographed on silica gel, elution being carried out with heptane and then with the gradient of the heptane/AcOEt mixture as far as (50/50; v/v). 0.325 g of the expected compound is obtained after crystallization from pentane.

EXAMPLE 9

Compound No. 25

5-(4-Chlorophenyl)-1-(2,4-dichlorophenyl)-3-(5-propyl-1,3,4-oxadiazol-2-yl)-1H-pyrazole-4-carbonitrile A mixture of 0.55 g of the compound obtained in Preparation 3.21 and 0.07 g of 4-toluenesulphonic acid monohydrate in 10 ml of toluene is heated at reflux overnight while removing the water formed using a Dean and Stark apparatus. After cooling to AT, the reaction mixture is diluted by addition of ether, the organic phase is washed with a 10% $NaHCO_3$ solution and dried over $MgSO_4$, and the solvent is evaporated under vacuum. The residue is chromatographed on silica gel, elution being carried out with heptane and then with the gradient of the heptane/AcOEt mixture as far as (70/30; v/v). 0.36 g of the expected compound is obtained after precipitation from isopropyl ether.

EXAMPLE 10

Compound No. 30

5-(4-Bromophenyl)-1-(2,4-dichlorophenyl)-3-(5-isopropyl-1,3,4-oxadiazol-2-yl)-1H-pyrazole-4-carbonitrile A mixture of 0.55 g of the compound obtained in Preparation 3.26 and 0.09 g of 4-toluenesulphonic acid monohydrate in 15 ml of toluene is heated at reflux for 3 hours while removing the water formed using a Dean and Stark apparatus. The reaction mixture is chromatographed on silica gel, elution being carried out with heptane and then with the gradient of the heptane/AcOEt mixture as far as (80/20; v/v). 0.37 g of the expected compound is obtained after precipitation from isopropyl ether.

EXAMPLE 11

Compound No. 39

2-[5-(4-Chlorophenyl)-1-(2,4-dichlorophenyl)-4-methyl-1H-pyrazol-3-yl]-5-(2-phenoxyethyl)-1,3,4-oxadiazole A mixture of 0.34 g of the compound from Preparation 3.35 and 3 ml of $POCl_3$ is heated at 100° C. for 1 hour 30 minutes. The reaction mixture is concentrated under vacuum, the residue is taken up in an ice-cold 10% $NaHCO_3$ solution and extracted with ether, the organic phase is washed with water and dried over $MgSO_4$, and the solvent is evaporated under vacuum. The residue is chromatographed on silica gel, elution being carried out with heptane and then with the gradient of the heptane/AcOEt mixture as far as (80/20; v/v). 0.11 g of the expected compound is obtained after crystallization from an ether/isopropyl ether mixture.

EXAMPLE 12

Compound No. 43

Ethyl 5-[5-(4-chlorophenyl)-1-(2,4-dichlorophenyl)-4-methyl-1H-pyrazol-3-yl]-1,3,4-oxadiazole-2-carboxylate A mixture of 12.5 g of the compound from Preparation 3.39 and 100 ml of $POCl_3$ is heated at 100° C. overnight. The reaction mixture is concentrated under vacuum, the residue is taken up in 100 ml of EtOH and cooled to 0° C., and the precipitate formed is filtered off and washed with EtOH and then with pentane. 7.98 g of the expected compound are obtained.

EXAMPLE 13

Compound No. 44

N-tert-Butyl-5-[5-(4-chlorophenyl)-1-(2,4-dichlorophenyl)-4-methyl-1H-pyrazol-3-yl]-1,3,4-oxadiazole-2-carboxamide A mixture of 0.5 g of the compound No. 43 and 5 ml of tert-butylamine in 3 ml of dioxane is left stirring at AT for 5 hours and is then heated at 60° C. for 48 hours. The reaction mixture is concentrated under vacuum and the residue is chromatographed on silica gel, elution being carried out with heptane and then with the gradient of the heptane/AcOEt mixture as far as (80/20; v/v). 0.32 g of the expected compound is obtained.

EXAMPLE 14

Compound No. 48

Ethyl 5-[5-(4-bromophenyl)-1-(2,4-dichlorophenyl)-4-ethyl-1H-pyrazol-3-yl]-1,3,4-oxadiazole-2-carboxylate A mixture of 3.7 g of the compound from Preparation 3.42 and 25 ml of $POCl_3$ is heated at 100° C. overnight. The reaction mixture is concentrated under vacuum, the residue is extracted with ether, the organic phase is washed with a 10% $NaHCO_3$ solution and dried over $MgSO_4$, and the solvent is evaporated under vacuum. The residue is taken up in EtOH and the crystalline product formed is filtered off and washed with EtOH and then with isopropyl ether. 2.34 g of the expected compound are obtained.

EXAMPLE 15

Compound No. 49

5-[5-(4-Bromophenyl)-1-(2,4-dichlorophenyl)-4-ethyl-1H-pyrazol-3-yl]-N,N-diethyl-1,3,4-oxadiazole-2-carboxamide A mixture of 0.5 g of the compound No. 48 and 0.24 ml of diethylamine in 5 ml of dioxane is left stirring at AT for 4 days. 1 ml of diethylamine is added and the mixture is heated at reflux for 24 hours. The reaction mixture is concentrated under vacuum and the residue is chromatographed on silica gel, elution being carried out with heptane and then with the gradient of the heptane/AcOEt mixture as far as (80/20; v/v). 0.34 g of the expected compound is obtained after precipitation from ether.

EXAMPLE 16

Compound No. 53

5-[5-(4-Bromophenyl)-1-(2,4-dichlorophenyl)-4-ethyl-1H-pyrazol-3-yl]-1,3,4-oxadiazole-2-thiol A mixture of 3 g of the compound from Preparation 2.3, 0.44 g of KOH pellets and 1.2 ml of carbon disulphide in 60 ml of EtOH is heated at reflux for 24 hours. The reaction mixture is concentrated under vacuum, the residue is taken up in water, ether is added, the mixture is left stirring for 10 minutes and the crystalline product formed is filtered off and washed with water and then with isopropyl ether. 2.99 g of the expected compound are obtained.

EXAMPLE 17

Compound No. 54

2-[5-(4-Bromophenyl)-1-(2,4-dichlorophenyl)-4-ethyl-1H-pyrazol-3-yl]-5-(isopropylthio)-1,3,4-oxadiazole A mixture of 0.62 g of the compound No. 53, 0.26 g of $K_2CO_3$ and 0.18 ml of 2-bromopropane in 6 ml of DMF is left stirring at AT overnight. 0.18 ml of 2-bromopropane and 0.2

EXAMPLE 18

Compound No. 55

2-[5-(4-Bromophenyl)-1-(2,4-dichlorophenyl)-4-ethyl-1H-pyrazol-3-yl]-5-(isopropylsulphonyl)-1,3,4-oxadiazole A mixture of 0.3 g of the compound No. 54 and 0.39 g of 3-chloroperbenzoic acid in 5 ml of DCM is left stirring for 24 hours. The reaction mixture is washed with a 10% NaHCO₃ solution, the organic phase is dried over MgSO₄ and the solvent is evaporated under vacuum. The residue is taken up in ethanol, the mixture is left stirring and the precipitate formed is filtered off and washed with ethanol and then with pentane. 0.23 g of the expected compound is obtained.

g of K₂CO₃ are again added and the mixture is left stirring at AT for 48 hours. The reaction mixture is poured onto 50 ml of water and extracted with AcOEt, the organic phase is washed with water and dried over MgSO₄, and the solvent is evaporated under vacuum. 0.45 g of the expected compound is obtained after crystallization from isopropyl ether.

EXAMPLE 19

Compound No. 62

2-(Benzylsulfinyl)-5-[5-(4-bromophenyl)-1-(2,4-dichlorophenyl)-4-ethyl-1H-pyrazol-3-yl]-1,3,4-oxadiazole A mixture of 0.4 g of the compound No. 61 and 0.21 g of 3-chloroperbenzoic acid in 10 ml of DCM is left stirring at AT for 1 hour 30 minutes. The reaction mixture is washed with a 10% NaHCO₃ solution, the organic phase is dried over MgSO₄ and the solvent is evaporated under vacuum. The residue is chromatographed on silica gel, elution being carried out with heptane and then with the gradient of the heptane/AcOEt mixture (70/30; v/v). 0.28 g of the expected compound is obtained after crystallization from ethanol.

The chemical structures and the physical properties of a few examples of compounds according to the invention are illustrated in the following table.

TABLE 2

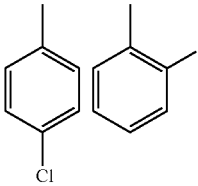

(I)

| Compound No. | $R_{1a}$ | $R_2$ | $R_3$ | $R_4$ | MH⁺; rt (min) NMR |
|---|---|---|---|---|---|
| 1 | —C(CH₃)₃ | —CH₃ | 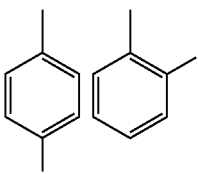 | 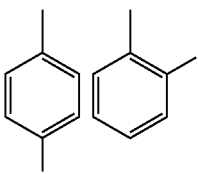 | 427; 11.20 |
| 2 (a) | —CH(CH₃)₂ | —CH₃ | 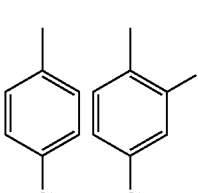 | 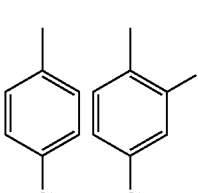 | 413; 10.79 |
| 3 | —C(CH₃)₃ | —CH₃ | |  | 461; 11.93 NMR |

TABLE 2-continued (I)

Structure: pyrazole with R2 at 4-position, R3 at 5-position, R4 on N1, connected at 3-position to 1,3,4-oxadiazole bearing R1a.

| Compound No. | R1a | R2 | R3 | R4 | MH+; rt (min) NMR |
|---|---|---|---|---|---|
| 4 (b) | —CH(CH₃)₂ | —CH₃ | 4-Cl-phenyl | 2,4-di-Cl-phenyl | 447; 11.58 |
| 5 (b) | —CH₂CH(CH₃)₂ | —CH₃ | 4-Cl-phenyl | 2,4-di-Cl-phenyl | 461; 11.72 |
| 6 (b) | —CH(CH₂CH₃)₂ | —CH₃ | 4-Cl-phenyl | 2,4-di-Cl-phenyl | 475; 12.35 |
| 7 (b) | —CH₂CH₂CH₂-phenyl | —CH₃ | 4-Cl-phenyl | 2,4-di-Cl-phenyl | 523; 12.52 NMR |
| 8 (b) | cyclohexyl | —CH₃ | 4-Cl-phenyl | 2,4-di-Cl-phenyl | 487; 12.49 |
| 9 (b) | 1-adamantyl | —CH₃ | 4-Cl-phenyl | 2,4-di-Cl-phenyl | 539; 13.53 |

TABLE 2-continued
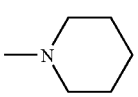
(I)
| Compound No. | R$_{1a}$ | R$_2$ | R$_3$ | R$_4$ | MH$^+$; rt (min) NMR |
|---|---|---|---|---|---|
| 10 |  | —CH$_3$ | 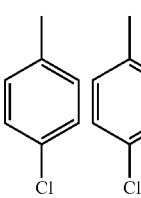 |  | 488; 11.54 |
| 11 | —NH$_2$ | —CH$_3$ |  | 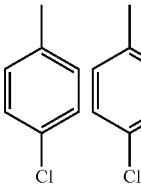 | 420; 9.59 |
| 12 | 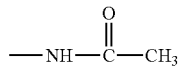 | —CH$_3$ |  | 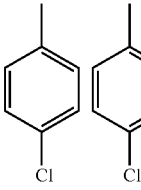 | 462; 9.67 |
| 13 | 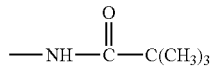 | —CH$_3$ |  | 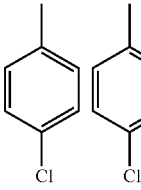 | 504; 10.76 |
| 14 | —CH$_3$ | —CH$_2$CH$_3$ |  |  | 477; 11.28 |
| 15 (c) | —CH(CH$_3$)$_2$ | —CH$_2$CH$_3$ | 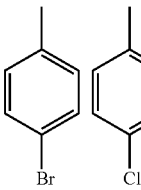 |  | 505; 12.11 |

TABLE 2-continued
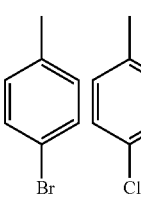
(I)
| Compound No. | R$_{1a}$ | R$_2$ | R$_3$ | R$_4$ | MH$^+$; rt (min) NMR |
|---|---|---|---|---|---|
| 16 (c) | —C(CH$_3$)$_3$ | —CH$_2$CH$_3$ | 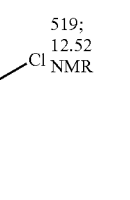 | 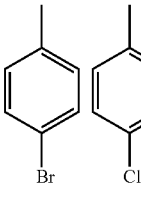 | 519; 12.52 NMR |
| 17 (c) | —CH(CH$_2$CH$_2$CH$_3$)$_2$ | —CH$_2$CH$_3$ | 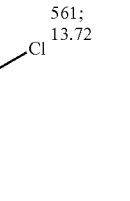 | 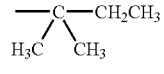 | 561; 13.72 |
| 18 (c) | 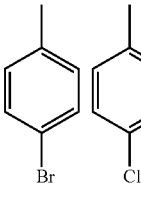 | —CH$_2$CH$_3$ | 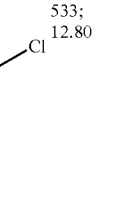 | 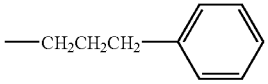 | 533; 12.80 |
| 19 (c) | —CH$_2$CH$_2$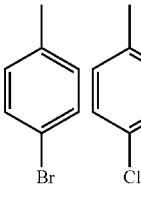 | —CH$_2$CH$_3$ | 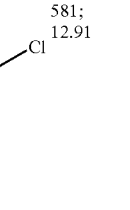 | 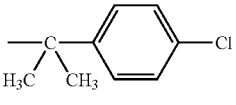 | 581; 12.91 |
| 20 (c) | 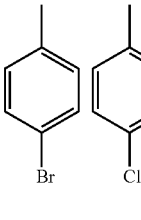 | —CH$_2$CH$_3$ |  |  | 615; 13.38 |
| 21 (c) | 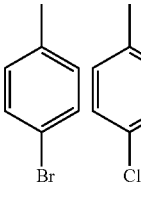 | —CH$_2$CH$_3$ |  | | 503; 11.82 |

TABLE 2-continued
(I)
| Compound No. | R$_{1a}$ | R$_2$ | R$_3$ | R$_4$ | MH$^+$; rt (min) NMR |
|---|---|---|---|---|---|
| 22 (c) | 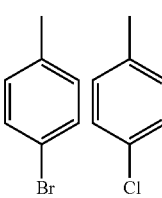 | —CH$_2$CH$_3$ | 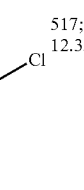 4-Br-C$_6$H$_4$ | 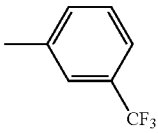 2,4-diCl-C$_6$H$_3$ | 517; 12.33 |
| 23 (c) | 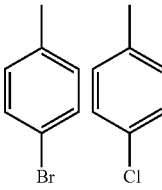 3-CF$_3$-C$_6$H$_4$ | —CH$_2$CH$_3$ | 4-Br-C$_6$H$_4$ | 2,4-diCl-C$_6$H$_3$ | 607; 13.29 |
| 24 | —N(CH$_3$)$_2$ | —CH$_2$CH$_3$ | 4-Br-C$_6$H$_4$ | 2,4-diCl-C$_6$H$_3$ | 506; 10.07 |
| 25 | —CH$_2$CH$_2$CH$_3$ | —CN | 4-Cl-C$_6$H$_4$ | 2,4-diCl-C$_6$H$_3$ | 458; 10.42 |
| 26 (d) | —CH(CH$_3$)$_2$ | —CN | 4-Cl-C$_6$H$_4$ | 2,4-diCl-C$_6$H$_3$ | 458; 11.12 |
| 27 (d) | —C(CH$_3$)$_3$ | —CN | 4-Cl-C$_6$H$_4$ | 2,4-diCl-C$_6$H$_3$ | 472; 11.48 |

TABLE 2-continued
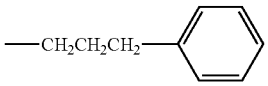
(I)
| Compound No. | $R_{1a}$ | $R_2$ | $R_3$ | $R_4$ | MH+; rt (min) NMR |
|---|---|---|---|---|---|
| 28 (d) | —CH$_2$CH$_2$CH$_2$— | —CN | 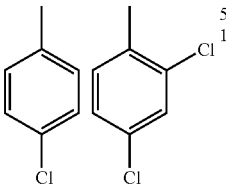 |  | 534; 11.97 |
| 29 (d) |  | —CN | 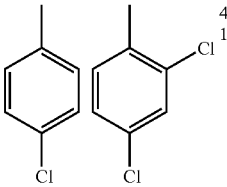 |  | 456; 10.83 |
| 30 | —CH(CH$_3$)$_2$ | —CN |  | 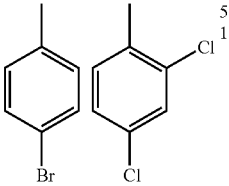 | 502; 11.22 |
| 31 (e) | —C(CH$_3$)$_3$ | —CN |  |  | 516; 11.57 |
| 32 (e) | —CH$_2$CH$_2$CH$_2$—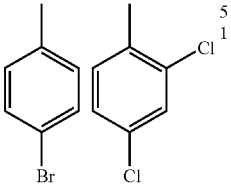 | —CN | 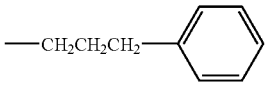 |  | 578; 12.05 |
| 33 (b) | —CH$_2$—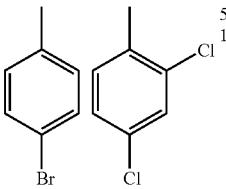 | —CH$_3$ | 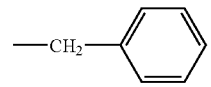 |  | 495; 11.94 |

TABLE 2-continued
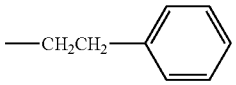
(I)
| Compound No. | $R_{1a}$ | $R_2$ | $R_3$ | $R_4$ | MH+; rt (min) NMR |
|---|---|---|---|---|---|
| 34 (b) | —CH$_2$CH$_2$—C$_6$H$_5$ | —CH$_3$ | 4-Cl-C$_6$H$_4$ | 2,4-Cl$_2$-C$_6$H$_3$ | 509; 12.15 NMR |
| 35 (b) | —CH$_2$CH$_2$—(3-F-C$_6$H$_4$) | —CH$_3$ | 4-Cl-C$_6$H$_4$ | 2,4-Cl$_2$-C$_6$H$_3$ | 527; 12.20 |
| 36 (b) | —CH$_2$CH$_2$—(3-Cl-C$_6$H$_4$) | —CH$_3$ | 4-Cl-C$_6$H$_4$ | 2,4-Cl$_2$-C$_6$H$_3$ | 543; 12.59 |
| 37 (b) | —CH$_2$CH$_2$—(4-CH$_3$-C$_6$H$_4$) | —CH$_3$ | 4-Cl-C$_6$H$_4$ | 2,4-Cl$_2$-C$_6$H$_3$ | 553; 12.31 |
| 38 (b) | —CH$_2$CH$_2$CH$_2$-(2-pyridyl) | —CH$_3$ | 4-Cl-C$_6$H$_4$ | 2,4-Cl$_2$-C$_6$H$_3$ | 537; 12.81 |
| 39 | —CH$_2$CH$_2$—O—C$_6$H$_5$ | —CH$_3$ | 4-Cl-C$_6$H$_4$ | 2,4-Cl$_2$-C$_6$H$_3$ | 525; 11.97 |

TABLE 2-continued
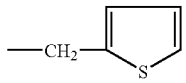
(I)
| Compound No. | $R_{1a}$ | $R_2$ | $R_3$ | $R_4$ | MH+; rt (min) NMR |
|---|---|---|---|---|---|
| 40 (b) | —CH₂—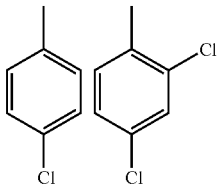 | —CH₃ | 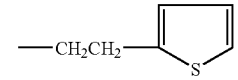 | 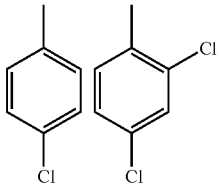 | 501; 11.86 |
| 41 (b) | —CH₂CH₂—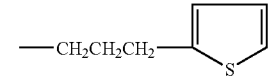 | —CH₃ | 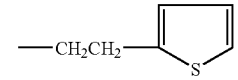 | 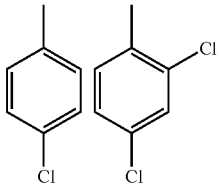 | 515; 12.06 |
| 42 (b) | —CH₂CH₂CH₂—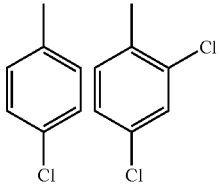 | —CH₃ | 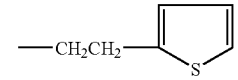 | 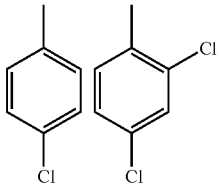 | 529; 12.40 |
| 43 | —COOCH₂CH₃ | —CH₃ | 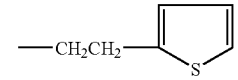 | 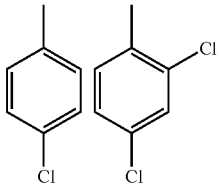 | 477; 11.54 |
| 44 | —CONHC(CH₃)₃ | —CH₃ | 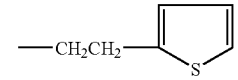 | 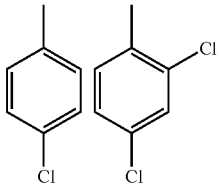 | 504; 11.64 |
| 45 (f) | —CON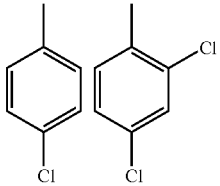 | —CH₃ | 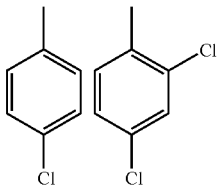 | 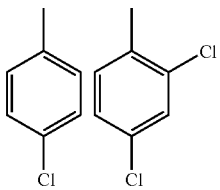 | 516; 11.70 |

TABLE 2-continued
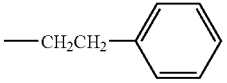
(I)
| Compound No. | R$_{1a}$ | R$_2$ | R$_3$ | R$_4$ | MH$^+$; rt (min) NMR |
|---|---|---|---|---|---|
| 46 (c) | —CH$_2$CH$_2$—C$_6$H$_5$ | —CH$_2$CH$_3$ | 4-Br-C$_6$H$_4$ | 2,4-Cl$_2$-C$_6$H$_3$ | 567; 12.67 |
| 47 (c) | —CH$_2$CH$_2$-(2-thienyl) | —CH$_2$CH$_3$ | 4-Br-C$_6$H$_4$ | 2,4-Cl$_2$-C$_6$H$_3$ | 573; 12.39 NMR |
| 48 | —COOCH$_2$CH$_3$ | —CH$_2$CH$_3$ | 4-Br-C$_6$H$_4$ | 2,4-Cl$_2$-C$_6$H$_3$ | |
| 49 | —CON(CH$_2$CH$_3$)$_2$ | —CH$_2$CH$_3$ | 4-Br-C$_6$H$_4$ | 2,4-Cl$_2$-C$_6$H$_3$ | 562; 12.22 |
| 50 (g) | —CO-piperidinyl | —CH$_2$CH$_3$ | 4-Br-C$_6$H$_4$ | 2,4-Cl$_2$-C$_6$H$_3$ | 574; 12.38 |
| 51 (g) | —CONH—CH$_2$—C$_6$H$_5$ | —CH$_2$CH$_3$ | 4-Br-C$_6$H$_4$ | 2,4-Cl$_2$-C$_6$H$_3$ | 596; 12.08 |

TABLE 2-continued
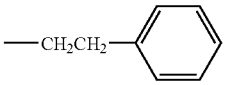
(I)
| Compound No. | $R_{1a}$ | $R_2$ | $R_3$ | $R_4$ | $MH^+$; rt (min) NMR |
|---|---|---|---|---|---|
| 52 (c) | —CH$_2$CH$_2$—C$_6$H$_5$ | —CN | 4-Br-C$_6$H$_4$ | 2,4-Cl$_2$-C$_6$H$_3$ | 564; 11.88 |
| 53 | —SH | —CH$_2$CH$_3$ | 4-Br-C$_6$H$_4$ | 2,4-Cl$_2$-C$_6$H$_3$ | 495; 11.40 |
| 54 | —S—CH(CH$_3$)$_2$ | —CH$_2$CH$_3$ | 4-Br-C$_6$H$_4$ | 2,4-Cl$_2$-C$_6$H$_3$ | 537; 12.99 |
| 55 | —SO$_2$—CH(CH$_3$)$_2$ | —CH$_2$CH$_3$ | 4-Br-C$_6$H$_4$ | 2,4-Cl$_2$-C$_6$H$_3$ | 569; 12.06 |
| 56 (h) | —S—CH$_2$CH(CH$_3$)$_2$ | —CH$_2$CH$_3$ | 4-Br-C$_6$H$_4$ | 2,4-Cl$_2$-C$_6$H$_3$ | 551; 13.35 NMR |

TABLE 2-continued (I) Structure: pyrazole (with R2 at 4-position, R3 at 5-position, R4 on N1) connected at 3-position to 1,3,4-oxadiazole bearing R1a.

| Compound No. | R1a | R2 | R3 | R4 | MH+; rt (min) NMR |
|---|---|---|---|---|---|
| 57 (h) | —S—CH(CH2CH3)2 | —CH2CH3 | 4-Br-phenyl | 2,4-diCl-phenyl | 565; 13.84 |
| 58 (i) | —SO2—CH(CH2CH3)2 | —CH2CH3 | 4-Br-phenyl | 2,4-diCl-phenyl | 597; 12.63 |
| 59 (h) | —S—CH2-cyclopropyl | —CH2CH3 | 4-Br-phenyl | 2,4-diCl-phenyl | 549; 12.91 NMR |
| 60 (i) | —SO2—CH2-cyclopropyl | —CH2CH3 | 4-Br-phenyl | 2,4-diCl-phenyl | 581; 12.24 |
| 61 (h) | —S—CH2-phenyl | —CH2CH3 | 4-Br-phenyl | 2,4-diCl-phenyl | 585; 13.14 |

TABLE 2-continued
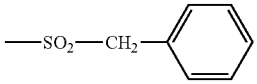
(I)
| Compound No. | R$_{1a}$ | R$_2$ | R$_3$ | R$_4$ | MH$^+$; rt (min) NMR |
|---|---|---|---|---|---|
| 62 |  | —CH$_2$CH$_3$ | 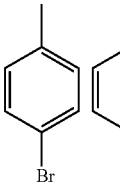 | 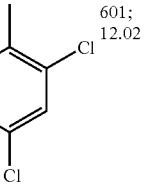 | 601; 12.02 |
| 63 (i) | 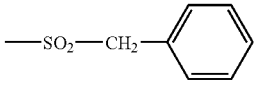 | —CH$_2$CH$_3$ |  | 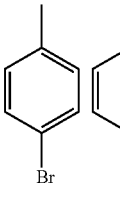 | 617; 12.29 |
| 64 (h) | 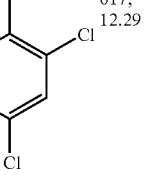 | —CH$_2$CH$_3$ | 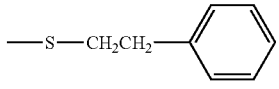 |  | 599; 13.38 |
| 65 (j) | 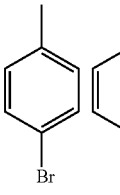 | —CH$_2$CH$_3$ | 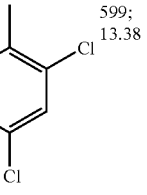 | 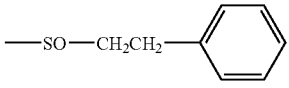 | 615; 12.20 |
| 66 (i) |  | —CH$_2$CH$_3$ | 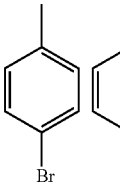 | 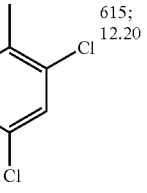 | 631; 12.53 |

TABLE 2-continued

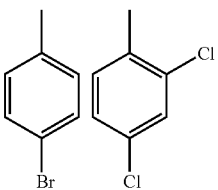
(I)

| Compound No. | $R_{1a}$ | $R_2$ | $R_3$ | $R_4$ | MH+; rt (min) NMR |
|---|---|---|---|---|---|
| 67 (k) | —SH | —CN | ![4-Br-phenyl] | ![2,4-Cl2-phenyl] | |
| 68 (l) | —S—CH(CH$_2$CH$_3$)$_2$ | —CN | ![4-Br-phenyl] | ![2,4-Cl2-phenyl] | 562; 12.67 |
| 69 (i) | —SO$_2$—CH(CH$_2$CH$_3$)$_2$ | —CN | ![4-Br-phenyl] | ![2,4-Cl2-phenyl] | 594; 11.62 |

(a) Compound prepared according to the procedure described in Example 1 from the corresponding compounds obtained in Preparations 3.
(b) Compound prepared according to the procedure described in Example 2 from the corresponding compounds obtained in Preparations 3.
(c) Compound prepared according to the procedure described in Example 7 from the corresponding compounds obtained in Preparations 3.
(d) Compound prepared according to the procedure described in Example 9 from the corresponding compounds obtained in Preparations 3.
(e) Compound prepared according to the procedure described in Example 10 from the corresponding compounds obtained in Preparations 3.
(f) Compound prepared according to the procedure described in Example 13 from the compound No. 43 and from the corresponding amines.
(g) Compound prepared according to the procedure described in Example 15 from the compound No. 48 and from the corresponding amines.
(h) Compound prepared according to the procedure described in Example 17 from the compound No. 53 and from the corresponding halogenated derivatives.
(i) Compound prepared according to the procedure described in Example 18 from the corresponding thio compound.
(j) Compound prepared according to the procedure described in Example 19 from the corresponding thio compound.
(k) Compound prepared according to the procedure described in Example 16.
(l) Compound prepared according to the procedure described in Example 17 from the compound No. 67 and from the corresponding halogenated derivatives.

Compound No. 3: ¹H NMR: d₆-DMSO: δ (ppm): 1.42, s, 9H; 2.33, s, 3H; 7.29, d, 2H; 7.49, d, 2H; 7.60, sd, 1H; 7.75-7.85, m, 2H.

Compound No. 7: ¹H NMR: d₆-DMSO: δ (ppm): 2.05, qt, 2H; 2.34, s, 3H; 2.70, t, 2H; 2.95, t, 2H; 7.10-7.35, m, 7H; 7.40-7.85, m, 5H.

Compound No. 16: ¹H NMR: d₆-DMSO: δ (ppm): 1.13, t, 3H; 1.41, s, 9H; 2.74, q, 2H; 7.24, d, 2H; 7.55-7.70, m, 3H; 7.76-7.86, m, 2H.

Compound No. 34: ¹H NMR: d₆-DMSO: δ (ppm): 2.32, s, 3H; 3.09, t, 2H; 3.28, t, 2H; 7.13-7.36, m, 7H; 7.50, d, 2H; 7.61, sd, 1H; 7.77, d, 1H; 7.82, d, 1H.

Compound No. 47: ¹H NMR: d₆-DMSO: δ (ppm): 1.12, t, 3H; 2.75, q, 2H; 3.23, mt, 4H; 6.93, mt, 2H; 7.23, d, 2H; 7.32, mt, 1H; 7.52-7.67, m, 3H; 7.72-7.81, m, 2H.

Compound No. 56: ¹H NMR: d₆-DMSO: δ (ppm): 1.00, d, 6H; 1.12, t, 3H; 2.03, spt, 1H; 2.73, q, 2H; 3.22, d, 2H; 7.24, d, 2H; 7.53-7.69, m, 3H; 7.73-7.85, m, 2H.

Compound No. 59: ¹H NMR: d₆-DMSO (250 MHz): δ (ppm): 0.36, mt, 2H; 0.58, mt, 2H; 1.12, t, 3H; 1.24, mt, 1H; 2.74, q, 2H; 3.27, d, 2H; 7.24, d, 2H; 7.53-7.69, m, 3H; 7.73-7.85, m, 2H.

EXAMPLE 20

Compound No. 70

5-[5-(4-Chlorophenyl)-1-(2,4-dichlorophenyl)-4-methyl-1H-pyrazol-3-yl]-3-isopropyl-1,2,4-oxadiazole A mixture of 1.15 g of the compound from Preparation 5.1 in 20 ml of n-butanol is heated at reflux overnight. After cooling to AT, the crystalline product formed is filtered off and washed with pentane. 0.77 g of the expected compound is obtained.

The chemical structures and the physical properties of a few examples of compounds according to the invention are illustrated in the following table.

TABLE 3

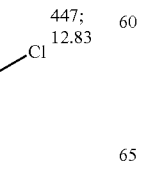

(I)

| Compound No. | $R_{1b}$ | $R_2$ | $R_3$ | $R_4$ | MH⁺; rt (min) NMR |
|---|---|---|---|---|---|
| 70 | —CH(CH₃)₂ | —CH₃ | 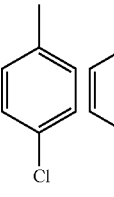 | 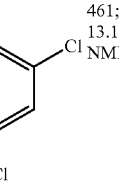 | 447; 12.83 |

TABLE 3-continued

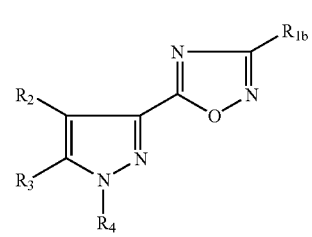

(I)

| Compound No. | $R_{1b}$ | $R_2$ | $R_3$ | $R_4$ | MH⁺; rt (min) NMR |
|---|---|---|---|---|---|
| 71 | —C(CH₃)₃ | —CH₃ | 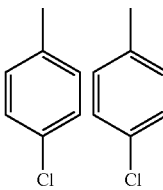 | | 461; 13.15 NMR |

(a) Compound prepared according to the procedure described in Example 20.

Compound No. 71: ¹H NMR: d₆-DMSO (250 MHz): 1.38, s, 9H; 2.35, s, 3H; 7.30, d, 2H; 7.50, d, 2H; 7.62, sd, 1H; 7.75-7.85, m, 2H.

EXAMPLE 21

Compound No. 72

5-(tert-Butyl)-3-[5-(4-chlorophenyl)-1-(2,4-dichlorophenyl)-4-methyl-1H-pyrazol-3-yl]-1,2,4-oxadiazole A mixture of 0.4 g of the compound from Preparation 7.1 in 10 ml of n-butanol is heated at reflux overnight. After cooling to AT, the crystalline product formed is filtered off. The crystalline product is chromatographed on silica gel, elution being carried out with heptane and then with the gradient of the heptane/AcOEt mixture as far as (90/10; v/v). 0.2 g of the expected compound is obtained.

The chemical structures and the physical properties of a few examples of compounds according to the invention are illustrated in the following table.

TABLE 4

(I)

[Structure: pyrazole ring with R2, R3, R4 substituents connected to 1,2,4-oxadiazole ring bearing R1c]

| Compound No. | R1c | R2 | R3 | R4 | MH+; rt (min) NMR |
|---|---|---|---|---|---|
| 72 | —C(CH$_3$)$_3$ | —CH$_3$ | 4-chlorophenyl | 2,4-dichlorophenyl | 461; 12.94 NMR |
| 73 (a) | —CH$_2$CH$_2$-phenyl | —CH$_3$ | 4-chlorophenyl | 2,4-dichlorophenyl | 509; 12.85 |
| 74 (a) | —CH$_2$CH$_2$-(2-thienyl) | —CH$_3$ | 4-chlorophenyl | 2,4-dichlorophenyl | 515; 12.68 |

(a) Compound prepared according to the procedure described in Example 21.

Compound No. 72: $^1$H NMR: d$_6$-DMSO (250 MHz): 1.44, s, 9H; 2.83, s, 3H; 7.29, d, 2H; 7.49, d, 2H; 7.60, sd, 1H; 7.76, d, 1H; 7.81, d, 1H.

The compounds of formula (I) have a very good in vitro affinity (IC$_{50}$≦5×10$^{-7}$M) for CB$_1$ cannabinoid receptors under the experimental conditions described by M. Rinaldi-Carmona et al. (FEBS Letters, 1994, 350, 240-244).

The antagonist nature of the compounds of formula (I) was demonstrated by the results obtained in the models of the inhibition of adenylate cyclase as described in M. Bouaboula et al., J. Biol. Chem., 1995, 270, 13973-13980, M. Rinaldi-Carmona et al., J. Pharmacol. Exp. Ther., 1996, 278, 871-878 and M. Bouaboula et al., J. Biol. Chem., 1997, 272, 22330-22339.

The toxicity of the compounds of formula (I) is compatible with their use as medicament.

Thus, according to another of its aspects, a subject-matter of the invention is medicaments which comprise a compound of formula (I) or a solvate or a hydrate of the compound of formula (I).

Thus, the compounds according to the invention can be used in man or in animals in the treatment or the prevention of diseases involving CB$_1$ cannabinoid receptors.

For example, and without implied limitation, the compounds of formula (I) are of use as psychotropic medicaments, in particular in the treatment of psychiatric disorders, including anxiety, depression, mood disorders, insomnia, delusional disorders, obsessive disorders, psychoses in general, schizophrenia or attention deficit hyperactivity disorders (ADHD) in hyperkinetic children (MBD), and in the treatment of disorders related to the use of psychotropic substances, in particular in the case of abuse of a substance and/or of dependency on a substance, including alcohol dependence and nicotine dependence.

The compounds of formula (I) according to the invention can be used as medicaments in the treatment of migraine, stress, illnesses of psychosomatic origin, panic attacks, epilepsy, movement disorders, in particular dyskinesias or Parkinson's disease, trembling and dystonia.

The compounds of formula (I) according to the invention can also be used as medicaments in the treatment of memory disorders, cognitive disorders, in particular in the treatment of senile dementia or Alzheimer's disease and in the treatment of disorders of attention or of vigilance. Furthermore, the compounds of formula (I) can be of use as neuroprotectants, in the treatment of ischemia, brain trauma and the treatment of neurodegenerative diseases, including chorea, Huntington's chorea or Tourette's syndrome.

The compounds of formula (I) according to the invention can be used as medicaments in the treatment of pain: neuropathic pain, acute peripheral pain or chronic pain of inflammatory origin.

The compounds of formula (I) according to the invention can be used as medicaments in the treatment of disorders of appetite, of appetency (for sugars, carbohydrates, drugs, alcohol or any appetizing substance) and/or of eating behavior, in particular in the treatment of obesity or of bulimia, as well as in the treatment of type II diabetes or non-insulin-dependent diabetes and in the treatment of dyslipidaemias of the metabolic syndrome. Thus, the compounds of formula (I) according to the invention are of use in the treatment of obesity and of the risks associated with obesity, in particular the cardiovascular risks. Furthermore, the compounds of formula (I) according to the invention can be used as medicaments in the treatment of gastrointestinal disorders, diarrhoea, ulcers, vomiting, bladder and urinary disorders, disorders of endocrine origin, cardiovascular disorders, hypotension, haemorrhagic shock, septic shock, chronic cirrhosis of the liver, hepatic steatosis, steatohepatitis, asthma, Raynaud's syndrome, glaucoma, fertility disorders, early pregnancy interruption, inflammatory phenomena, diseases of the immune system, in particular autoimmune and neuroinflammatory diseases, such as rheumatoid arthritis, reactive arthritis, diseases which bring about demyelination, multiple sclerosis, infectious and viral diseases, such as encephalitis, or strokes and as medicaments for anticancer chemotherapy, in the treatment of Guillain-Barré syndrome and in the treatment of osteoporosis.

According to the present invention, the compounds of formula (I) are very particularly of use in the treatment of psychotic disorders, in particular schizophrenia or attention deficit hyperactivity disorders (ADHD) in hyperkinetic children (MBD); in the treatment of disorders of appetite and of obesity; in the treatment of memory and cognitive deficiencies; or in the treatment of alcohol dependence or nicotine dependence, that is to say for weaning from alcohol and for weaning from tobacco.

According to one of its aspects, the present invention relates to the use of a compound of formula (I) and of its solvates or hydrates in the treatment of the disorders and diseases indicated above.

According to another of its aspects, the present invention relates to pharmaceutical compositions comprising, as active principle, a compound according to the invention. These pharmaceutical compositions comprise an effective dose of at least one compound according to the invention or one solvate or hydrate of the said compound and at least one pharmaceutically acceptable excipient.

The said excipients are chosen, according to the pharmaceutical form and the method of administration desired, from the usual excipients which are known to a person skilled in the art.

The pharmaceutical compositions according to the present invention can comprise, in addition to a compound of formula (I), one (or more) other active principles of use in the treatment of the disorders and diseases indicated above.

Thus, another subject-matter of the present invention is pharmaceutical compositions comprising a compound of formula (I) according to the present invention in combination with one (or more) active principles chosen from one of the following therapeutic categories:

an angiotensin II $AT_1$ receptor antagonist, alone or in combination with a diuretic;
a converting enzyme inhibitor, alone or in combination with a diuretic or a calcium antagonist;
a calcium antagonist;
a beta-blocker, alone or in combination with a diuretic or with a calcium antagonist;
an antihyperlipidaemic or an antihypercholesterolaemic;
an antidiabetic;
another antiobesity agent;
a nicotinic agonist or a partial nicotinic agonist;
an antidepressant or an antipsychotic;
an antineoplastic or an antiproliferative agent;
an opioid antagonist;

and:
an agent of use in the treatment of alcoholism or symptoms of weaning;
an agent of use in the treatment of osteoporosis;
a nonsteroidal or steroidal anti-inflammatory;
an anti-infective;
an analgesic.

The term "angiotensin II $AT_1$ receptor antagonist" is understood to mean a compound such as candesartan cilexitil, eprosartan, irbesartan, losartan potassium, olmesartan medoxomil, telmisartan or valsartan, it being possible for each of these compounds to be itself combined with a diuretic, such as hydrochlorothiazide.

The term "converting enzyme inhibitor" is understood to mean a compound such as alacepril, benazepril, captopril, cilazapril, enalapril, enalaprilat, fosinopril, imidapril, lisinopril, moexipril, perindopril, quinapril, ramipril, spirapril, temocapril, trandolapril or zofenopril, it being possible for each of these compounds to be itself combined with a diuretic, such as hydrochlorothiazide or indapamide, or with a calcium antagonist, such as amlodipine, diltiazem, felodipine or verapamil.

The term "calcium antagonist" is understood to mean a compound such as amlodipine, aranidipine, benidipine, bepridil, cilnidipine, diltiazem, efonidipine hydrochloride ethanol, fasudil, felodipine, isradipine, lacidipine, lercanidipine hydrochloride, manidipine, mibefradil hydrochloride, nicardipine, nifedipine, nilvadipine, nimodipine, nisoldipine, nitrendipine, terodiline or verapamil.

The term "beta-blocker" is understood to mean a compound such as acebutolol, alprenolol, amosulalol, arotinolol, atenolol, befunolol, betaxolol, bevantolol, bisoprolol, bopindolol, bucumolol, bufetolol, bunitrolol, butofilolol, carazolol, carteolol, carvedilol, cloranolol, epanolol, esmolol, indenolol, labetalol, landiolol, levobunolol, levomoprolol, mepindolol, metipranolol, metoprolol, nadolol, nebivolol, nifenalol, nipradilol, oxprenolol, penbutolol, pindolol, propranolol, salmeterol, sotalol, talinolol, tertatolol, tilisolol, timolol, xamoterol or xibenolol.

The term "antihyperlipidaemic" or "antihypercholesterolaemic" is understood to mean a compound chosen from fibrates, such as alufibrate, beclobrate, bezafibrate, ciprofibrate, clinofibrate, clofibrate, etofibrate or fenofibrate; statins (HMG-CoA reductase inhibitors), such as atorvastatin, fluvastatin sodium, lovastatin, pravastatin, rosuvastatin or simvastatin, or a compound such as acipimox, aluminum nicotinate, azacosterol, cholestyramine, dextrothyroxine, meglutol, niceritrol, nicoclonate, nicotinic acid, beta-sitosterol or tiadenol.

The term "antidiabetic" is understood to mean a compound belonging to one of the following categories: sulfonylureas, biguanidines, alpha-glucosidase inhibitors, thiazolidinedione or metiglinides, such as acarbose, acetohexamide, carbutamide, chlorpropamide, glibenclamide, glibomuride, gliclazide, glimepiride, glipizide, gliquidone, glisoxepide, glybuzole, glymidine, metahexamide, metformin, miglitol, nateglinide, pioglitazone, repaglinide, rosiglitazone, tolazamide, tolbutamide, troglitazone or voglibose, and also insulin and insulin analogues.

The term "other antiobesity agent", is understood to mean a compound such as amfepramone, benfluorex, benzphetamine, indanorex, mazindole, mefenorex, methamphetamine, D-norpseudoephedrine or sibutramine, a lipase inhibitor (orlistat cetilistat), a PPAR agonist, a dopamine agonist, a leptin receptor agonist, a serotonin receptor inhibitor, a beta-3 agonist, a CCK-A agonist, an NPY inhibitor, an MC4 receptor agonist or a bombesin agonist.

The term "opioid antagonist" is understood to mean a compound such as naltrexone, naloxone or nalmefene.

The term "agent of use in the treatment of alcoholism and symptoms of weaning" is understood to mean acamprosate, benzodiazepines, beta-blockers, clonidine or carbamazepine.

The term "agent of use in the treatment of osteoporosis" is understood to mean, for example, biphosphonates, such as etidronate, clodronate, tiludronate or risedronate.

In the pharmaceutical compositions of the present invention for oral, sublingual, subcutaneous, intramuscular, intravenous, topical, local, intratracheal, intranasal, transdermal or rectal administration, the active principle of formula (I) above or its optional salt, solvate or hydrate can be administered in unit administration form, as a mixture with conventional pharmaceutical excipients, to animals and to human beings for the prophylaxis or the treatment of the above disorders or diseases.

The appropriate unit administration forms comprise oral forms, such as tablets, soft or hard gelatin capsules, powders, granules and oral solutions or suspensions, sublingual, buccal, intratracheal, intraocular or intranasal administration forms, forms for administration by inhalation, topical, transdermal, subcutaneous, intramuscular or intravenous administration forms, rectal administration forms and implants. For the topical application, the compounds according to the invention can be used in creams, gels, ointments or lotions.

By way of example, a unit administration form of a compound according to the invention in the tablet form can comprise the following components:

| | |
|---|---|
| Compound according to the invention | 50.0 mg |
| Mannitol | 223.75 mg |
| Sodium croscarmellose | 6.0 mg |
| Maize starch | 15.0 mg |
| Hydroxypropylmethylcellulose | 2.25 mg |
| Magnesium stearate | 3.0 mg |

Orally, the dose of active principle administered per day can reach 0.01 to 100 mg/kg, taken one or more times, preferably 0.02 to 50 mg/kg.

There may be specific cases where higher or lower dosages are appropriate: such dosages do not depart from the scope of the invention. According to the usual practice, the dosage appropriate to each patient is determined by the doctor according to the method of administration and the weight and the response of the said patient.

The present invention, according to another of its aspects, also relates to a method for the treatment of the pathologies indicated above which comprises the administration, to a patient, of an effective dose of a compound according to the invention or one of its pharmaceutically acceptable salts or hydrates or solvates.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A compound of the formula (I):

in which:

$R_1$ represents a heterocyclic radical chosen from:

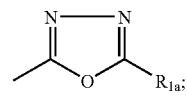

$R_{1a}$ represents:

a $(C_1-C_7)$alkyl which is unsubstituted or substituted by:
  a) one or more halogen atoms;
  b) a $(C_1-C_4)$alkoxy, a trifluoromethoxy or a phenoxy;
  c) a phenyl which is unsubstituted or mono-, di- or trisubstituted by substituents chosen independently from a halogen atom, a $(C_1-C_4)$alkyl, a $(C_1-C_4)$alkoxy, a trifluoromethyl radical or a trifluoromethoxy radical; or
  d) an aromatic heterocyclic radical chosen from a thienyl, a pyrrolyl, an imidazolyl, a furyl or a pyrazolyl;

a nonaromatic $C_3-C_{12}$ carbocyclic radical which is unsubstituted or substituted one or more times by a $(C_1-C_4)$alkyl;

a phenyl which is unsubstituted or mono-, di- or trisubstituted by substituents chosen independently from a halogen atom, a $(C_1-C_4)$alkyl, a $(C_1-C_4)$alkoxy, a trifluoromethyl radical or a trifluoromethoxy radical;

an —$NR_5R_6$ group;
an —$NR_7COR_8$ group;
a —$COOR_9$ group;
a —$CONR_{10}R_{11}$ group;
an —S—$R_{12}$ group;
an —$S(O)_mR_{13}$ group in which m is 1 or 2;
an —O—$R_{14}$ group;

$R_2$ represents a $(C_1-C_5)$alkyl or a cyano;

$R_3$ represents a phenyl which is unsubstituted or mono-, di- or trisubstituted by substituents chosen independently from a halogen atom, a $(C_1-C_4)$alkyl, a $(C_1-C_4)$alkoxy, a trifluoromethyl radical, a trifluoromethoxy radical or an $S(O)_n$Alk group;

$R_4$ represents a phenyl which is unsubstituted or mono-, di- or trisubstituted by substituents chosen independently from a halogen atom, a $(C_1-C_4)$alkyl, a $(C_1-C_4)$alkoxy, a trifluoromethyl radical, a trifluoromethoxy radical or an $S(O)_n$Alk group;

$R_5$ and $R_6$ each independently represent a hydrogen atom or a $(C_1-C_4)$alkyl;

or else $R_5$ and $R_6$, together with the nitrogen atom to which they are bonded, constitute a heterocyclic radical chosen from azetidine, pyrrolidine, piperidine or morpholine;

$R_7$ represents a hydrogen atom or a $(C_1-C_3)$alkyl;

$R_8$ represents a $(C_1-C_4)$alkyl;

$R_9$ represents a $(C_1-C_4)$alkyl;

$R_{10}$ and $R_{11}$ each independently represent a hydrogen atom, a $(C_1-C_4)$alkyl or a benzyl;

or else $R_{10}$ and $R_{11}$, together with the nitrogen atom to which they are bonded, constitute a heterocyclic radical chosen from azetidine, pyrrolidine, piperidine or morpholine;

$R_{12}$ represents a hydrogen atom, a $(C_1-C_7)$alkyl, a $(C_3-C_7)$cycloalkyl, a $(C_3-C_7)$cycloalkylmethyl, a benzyl or a phenethyl;

$R_{13}$ represents a $(C_1-C_7)$alkyl, a $(C_3-C_7)$cycloalkyl, a $(C_3-C_7)$cycloalkylmethyl, a benzyl or a phenethyl;

$R_{14}$ represents a $(C_1-C_7)$alkyl or a phenyl which is unsubstituted or mono-, di- or trisubstituted by substituents chosen independently from a halogen atom, a $(C_1-C_4)$alkyl, a $(C_1-C_4)$alkoxy, a trifluoromethyl radical or a trifluoromethoxy radical;

n represents 0, 1 or 2; and

Alk represents a $(C_1-C_4)$alkyl.

2. The compound of formula (I) according to claim 1, wherein:

$R_1$ represents a radical:

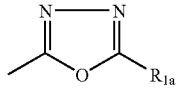

$R_{1a}$ represents:

a methyl, a propyl, an isopropyl, a 1,1-dimethylpropyl, a 1-ethylpropyl, a 3-phenylpropyl, an isobutyl, a tert-butyl, a 1-propylbutyl, a chlorophenyl)-1-methylethyl, a 2-phenylethyl, a 2-(3-fluorophenyl)ethyl, a 2-(3-chlorophenyl)ethyl, a benzyl, a 3-(4-methoxyphenyl)propyl, a 4-phenylbutyl, a 2-phenoxyethyl, a (2-thienyl)methyl, a 2-(2-thienyl)ethyl or a 3-(2-thienyl)propyl;

a cyclopropyl, a cyclobutyl, a cyclohexyl or a 1-adamantyl;

a 3-(trifluoromethyl)phenyl;

an amino, a dimethylamino or a piperid-1-yl;

an acetylamino or a pivaloylamino;

an ethoxycarbonyl;

a tert-butylaminocarbonyl, a diethylaminocarbonyl, a benzylaminocarbonyl or a piperid-1-ylcarbonyl;

a mercapto, an isopropylthio, an isobutylthio, a (1-ethylpropyl)thio, a (cyclopropylmethyl)thio, a benzylthio or a 2-phenylethylthio;

a benzylsulfinyl, a (2-phenylethyl)sulfinyl, an isopropylsulfonyl, a (1-ethylpropyl)sulfonyl, a (cyclopropylmethyl)sulfonyl, a benzylsulfonyl or a (2-phenylethyl)sulfonyl;

$R_2$ represents a methyl, an ethyl or a cyano;

$R_3$ represents a 4-bromophenyl or a 4-chlorophenyl; and $R_4$ represents a 2-chlorophenyl or a 2,4-dichlorophenyl.

3. The compound of formula (I) according to claim 1 chosen from:

2-(tert-butyl)-5-[1-(2-chlorophenyl)-5-(4-chlorophenyl)-4-methyl-1H-pyrazol-3-yl]-1,3,4-oxadiazole;

2-[1-(2-chlorophenyl)-5-(4-chlorophenyl)-4-methyl-1H-pyrazol-3-yl]-5-isopropyl-1,3,4-oxadiazole;

2-(tert-butyl)-5-[5-(4-chlorophenyl)-1-(2,4-dichlorophenyl)-4-methyl-1H-pyrazol-3-yl]-1,3,4-oxadiazole;

2-[5-(4-chlorophenyl)-1-(2,4-dichlorophenyl)-4-methyl-1H-pyrazol-3-yl]-5-isopropyl-1,3,4-oxadiazole;

2-[5-(4-chlorophenyl)-1-(2,4-dichlorophenyl)-4-methyl-1H-pyrazol-3-yl]-5-isobutyl-1,3,4-oxadiazole;

2-[5-(4-chlorophenyl)-1-(2,4-dichlorophenyl)-4-methyl-1H-pyrazol-3-yl]-5-(1-ethylpropyl)-1,3,4-oxadiazole;

2-[5-(4-chlorophenyl)-1-(2,4-dichlorophenyl)-4-methyl-1H-pyrazol-3-yl]-5-(3-phenylpropyl)-1,3,4-oxadiazole;

2-[5-(4-chlorophenyl)-1-(2,4-dichlorophenyl)-4-methyl-1H-pyrazol-3-yl]-5-cyclohexyl-1,3,4-oxadiazole;

2-(1-adamantyl)-5-[5-(4-chlorophenyl)-1-(2,4-dichlorophenyl)-4-methyl-1H-pyrazol-3-yl]-1,3,4-oxadiazole;

1-[5-[5-(4-chlorophenyl)-1-(2,4-dichlorophenyl)-4-methyl-1H-pyrazol-3-yl]-1,3,4-oxadiazol-2-yl]piperidine;

5-[5-(4-chlorophenyl)-1-(2,4-dichlorophenyl)-4-methyl-1H-pyrazol-3-yl]-1,3,4-oxadiazol-2-amine;

N-[5-[5-(4-chlorophenyl)-1-(2,4-dichlorophenyl)-4-methyl-1H-pyrazol-3-yl]-1,3,4-oxadiazol-2-yl]acetamide;

N-[5-[5-(4-chlorophenyl)-1-(2,4-dichlorophenyl)-4-methyl-1H-pyrazol-3-yl]-1,3,4-oxadiazol-2-yl]-2,2-dimethylpropanamide;

2-[5-(4-bromophenyl)-1-(2,4-dichlorophenyl)-4-ethyl-1H-pyrazol-3-yl]-5-methyl-1,3,4-oxadiazole;

2-[5-(4-bromophenyl)-1-(2,4-dichlorophenyl)-4-ethyl-1H-pyrazol-3-yl]-5-isopropyl-1,3,4-oxadiazole;

2-[5-(4-bromophenyl)-1-(2,4-dichlorophenyl)-4-ethyl-1H-pyrazol-3-yl]-5-(tert-butyl)-1,3,4-oxadiazole;

2-[5-(4-bromophenyl)-1-(2,4-dichlorophenyl)-4-ethyl-1H-pyrazol-3-yl]-5-(1-propylbutyl)-1,3,4-oxadiazole;

2-[5-(4-bromophenyl)-1-(2,4-dichlorophenyl)-4-ethyl-1H-pyrazol-3-yl]-5-(1,1-dimethylpropyl)-1,3,4-oxadiazole;

2-[5-(4-bromophenyl)-1-(2,4-dichlorophenyl)-4-ethyl-1H-pyrazol-3-yl]-5-(3-phenylpropyl)-1,3,4-oxadiazole;

2-[5-(4-bromophenyl)-1-(2,4-dichlorophenyl)-4-ethyl-1H-pyrazol-3-yl]-5-[1-(4-chlorophenyl)-1-methylethyl]-1,3,4-oxadiazole;

2-[5-(4-bromophenyl)-1-(2,4-dichlorophenyl)-4-ethyl-1H-pyrazol-3-yl]-5-cyclopropyl-1,3,4-oxadiazole;

2-[5-(4-bromophenyl)-1-(2,4-dichlorophenyl)-4-ethyl-1H-pyrazol-3-yl]-5-cyclobutyl-1,3,4-oxadiazole;

2-[5-(4-bromophenyl)-1-(2,4-dichlorophenyl)-4-ethyl-1H-pyrazol-3-yl]-5-[3-(trifluoromethyl)phenyl]-1,3,4-oxadiazole;

2-[5-(4-bromophenyl)-1-(2,4-dichlorophenyl)-4-ethyl-1H-pyrazol-3-yl]-N,N-dimethyl-1,3,4-oxadiazole-2-amine;

5-(4-chlorophenyl)-1-(2,4-dichlorophenyl)-3-(5-propyl-1,3,4-oxadiazol-2-yl)-1H-pyrazole-4-carbonitrile;

5-(4-chlorophenyl)-1-(2,4-dichlorophenyl)-3-(5-isopropyl-1,3,4-oxadiazol-2-yl)-1H-pyrazole-4-carbonitrile;

3-(5-(tert-butyl)-1,3,4-oxadiazol-2-yl)-5-(4-chlorophenyl)-1-(2,4-dichlorophenyl)-1H-pyrazole-4-carbonitrile;

5-(4-chlorophenyl)-1-(2,4-dichlorophenyl)-3-[5-(3-phenylpropyl)-1,3,4-oxadiazol-2-yl]-1H-pyrazole-4-carbonitrile;

5-(4-chlorophenyl)-3-(5-cyclopropyl-1,3,4-oxadiazol-2-yl)-1-(2,4-dichlorophenyl)-1H-pyrazole-4-carbonitrile;

5-(4-bromophenyl)-1-(2,4-dichlorophenyl)-3-(5-isopropyl-1,3,4-oxadiazol-2-yl)-1H-pyrazole-4-carbonitrile;

5-(4-bromophenyl)-3-(5-(tert-butyl)-1,3,4-oxadiazol-2-yl)-1-(2,4-dichlorophenyl)-1H-pyrazole-4-carbonitrile;

5-(4-bromophenyl)-1-(2,4-dichlorophenyl)-3-(5-(3-phenylpropyl)-1,3,4-oxadiazol-2-yl]-1H-pyrazole-4-carbonitrile;

2-[5-(4-chlorophenyl)-1-(2,4-dichlorophenyl)-4-methyl-1H-pyrazol-3-yl]-5-(2-phenylethyl)-1,3,4-oxadiazole;
2-[5-(4-bromophenyl)-1-(2,4-dichlorophenyl)-4-ethyl-1H-pyrazol-3-yl]-5-[2-(2-thienyl)ethyl]-1,3,4-oxadiazole;
2-[5-(4-bromophenyl)-1-(2,4-dichlorophenyl)-4-ethyl-1H-pyrazol-3-yl]-5-(isobutylthio)-1,3,4-oxadiazole; and
2-[5-(4-bromophenyl)-1-(2,4-dichlorophenyl)-4-ethyl-1H-pyrazol-3-yl]-5-[(cyclopropylmethyl)thio]-1,3,4-oxadiazole.

4. A pharmaceutical composition comprising a compound of formula (I) according to claim 1 and at least one pharmaceutically acceptable excipient.

5. A pharmaceutical composition comprising a compound of formula (I) according to claim 2 and at least one pharmaceutically acceptable excipient.

6. A pharmaceutical composition comprising a compound of formula (I) according to claim 3 and at least one pharmaceutically acceptable excipient.

\* \* \* \* \*

UNITED STATES PATENT AND TRADEMARK OFFICE
CERTIFICATE OF CORRECTION

PATENT NO. : 7,632,852 B2
APPLICATION NO. : 11/835670
DATED : December 15, 2009
INVENTOR(S) : Francis Barth et al.

It is certified that error appears in the above-identified patent and that said Letters Patent is hereby corrected as shown below:

In column 1, line 40-46, delete " 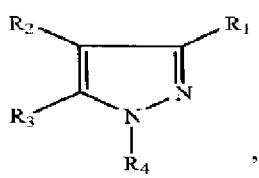 " and insert -- 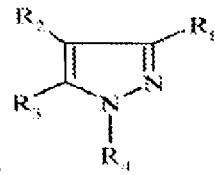 --, therefor.

In column 9, line 34, delete "$R_1 =$" and insert -- $R_1 =$ --, therefor.

In column 11, line 61, delete "$R_1 =$" and insert -- $R_1 =$ --, therefor.

In column 12, line 39, delete "$R_1 =$" and insert -- $R_1 =$ --, therefor.

In column 18, line 38, delete "LC/UVAMS" and insert -- LC/UV/MS --, therefor.

In column 26, line 35, delete "oxo)acetate" and insert -- (oxo)acetate --, therefor.

In column 26, line 65, delete "(TI)" and insert -- (II) --, therefor.

In column 79, line 11, delete "dyslipidaemias" and insert -- dyslipidemias --, therefor.

In column 80, line 20, delete "cilexitil," and insert -- cilexetil, --, therefor.

In column 80, line 64, delete "metiglinides," and insert -- mitiglinides, --, therefor.

In column 80, line 65, delete "glibomuride," and insert -- glibornuride, --, therefor.

In column 82, line 9-14, in claim 1, delete " 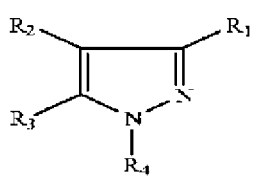 " and insert -- 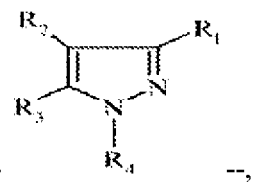 --, therefor.

In column 83, line 34, in claim 2, delete "chlorophenyl)" and insert -- 1-(4-chlorophenyl) --, therefor.

In column 84, line 66, in claim 3, delete "yl]" and insert -- yl) --, therefor.

Signed and Sealed this
Twenty-third Day of August, 2011

David J. Kappos
*Director of the United States Patent and Trademark Office*